United States Patent [19]

Nakamura et al.

[11] Patent Number: 4,886,813

[45] Date of Patent: Dec. 12, 1989

[54] PROLINE DERIVATIVES

[75] Inventors: Shizuo Nakamura, Naruto; Makoto Inoue, Tokushima; Masatoshi Inai, Tokushima; Yoshiaki Tsuda, Anan, all of Japan

[73] Assignee: Otsuka Pharmaceutical Factory, Inc., Naruto, Japan

[21] Appl. No.: 856,901

[22] Filed: Apr. 28, 1986

[30] Foreign Application Priority Data

Nov. 13, 1985 [JP] Japan .................... 60-254341
Nov. 13, 1985 [JP] Japan .................... 60-254342
Apr. 18, 1986 [JP] Japan .................... 61-90803

[51] Int. Cl.$^4$ .................... A61K 31/395; C07D 401/12
[52] U.S. Cl. .................... 514/326; 514/423; 514/343; 514/183; 514/212; 514/255; 514/316; 514/318; 514/422; 548/553; 548/517; 548/518; 546/281; 546/208; 546/197; 540/480; 540/598; 540/602; 544/372; 544/360
[58] Field of Search .................... 548/553, 518, 517; 514/423, 163, 212, 255, 316, 318, 326, 422, 343; 546/208, 187, 197, 281; 540/480, 598, 602; 544/372, 360

[56] References Cited

U.S. PATENT DOCUMENTS 4,642,355 2/1987 Nakamura et al. .................... 548/533

FOREIGN PATENT DOCUMENTS 3506307 9/1985 Fed. Rep. of Germany ...... 548/533
2158444 1/1985 United Kingdom ................ 548/533

OTHER PUBLICATIONS

Chemical Abstracts vol. 105 (1986), Item 173,052, Abstracting German Offenlegungsschrift DE 3,506,307, Sep. 5, 1985 (119 pages).

*Primary Examiner*—Robert T. Bond
*Attorney, Agent, or Firm*—Armstrong, Nikaido, Marmelstein, Kubovcik & Murray

[57] ABSTRACT

Disclosed is a proline derivative of the formula

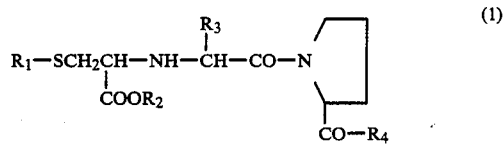

or a pharmaceutically acceptable salt thereof. These derivatives have useful utilities such as activity of inhibiting angiotensin converting enzyme.

21 Claims, No Drawings

PROLINE DERIVATIVES

This invention relates to novel proline derivatives and salts thereof.

The proline derivatives of this invention are represented by the formula (1)

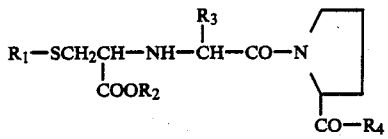

wherein:
$R_1$ is adamantyl, benzocyloalkyl or cycloalkyl optionally substituted with lower alkyl, or $R_1$ is $C_1$-$C_9$ alkyl or a group

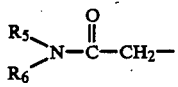

(wherein $R_5$ and $R_6$ are the same or different and each represent hydrogen, lower alkyl, phenyl, phenyl-lower alkyl, naphthyl or cycloalkyl, or $R_5R_6N$- is

wherein R is alkylene);
$R_2$ is hydrogen or lower alkyl;
$R_3$ is lower alkyl; and
$R_4$ is hydroxy, lower alkoxy, a group

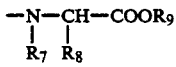

(wherein $R_7$ is hydrogen, and $R_8$ is hydrogen, lower alkyl or phenyl-lower alkyl, or $R_7$ and $R_8$ are taken together and form $C_2$-$C_4$ alkylene bridge, and $R_9$ is hydrogen or lower alkyl), or substituted lower alkoxy wherein the substituent is selected from the group consisting of lower alkoxy, lower alkoxy-carbonyl, halogen, carbamoyl, arylcarbamoyl, pyridyl, a group

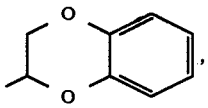

4-(1,1-diphenylmethyl)-1-piperazinyl and lower alkoxycarbonylamino, or $R_4$ is aryloxy, tocopheryloxy, 1-(aryl-lower alkyl)-piperidyloxy, amino, lower alkoxycarbonyl-substituted arylamino, lower alkylsulfonylamino or arylsulfonylamino, with the proviso that $R_4$ is not hydroxy or lower alkoxy when $R_1$ is $C_1$-$C_9$ alkyl.

Throughout the specification and claims, the term "lower alkyl" and the term "lower alkoxy" used as they are or as present in other groups refer to straight chain or branched chain alkyl having 1 to 6 carbon atoms (such as methyl, ethyl, isopropyl, isobutyl, 1-methylpropyl, t-butyl, pentyl, isoamyl, neopentyl, hexyl, etc.) and straight chain or branched chain alkoxy having 1 to 6 carbon atoms (such as methoxy, ethoxy, isopropoxy, isobutoxy, 1-methylpropoxy, t-butoxy, pentyloxy, isoamyloxy, neopentyloxy, hexyloxy, etc.), respectively.

Given below are examples of groups represented by $R$, $R_1$, $R_2$, $R_3$, $R_4$, $R_5$, $R_6$, $R_7$, $R_8$, and $R_9$ in the formula (1) and the corresponding respective groups in the other formulas to be described later.

Examples of benzocycloalkyl groups are 1-indanyl, 2-indanyl, 1,2,3,4-tetrahydro-1-naphthyl, 1,2,3,4-tetrahydro-2-naphthyl, etc.

Examples of cycloalkyl groups optionally substituted with lower alkyl are cycloalkyl groups having 3 to 8 carbon atoms such as cyclopropyl, cyclobutyl, cyclopentyl, cyclohexyl, cycloheptyl, cylcooctyl, etc. and cycloalkyl groups having 3 to 8 carbon atoms and substituted with lower alkyl group such as 1-methylcyclopropyl, 1-methylcyclobutyl, 1-methylcyclopentyl, 1-methylcyclohexyl, 1,3-dimethylcyclohexyl, 1,4-dimethylcyclohexyl, 1-methylcycloheptyl, etc.

Examples of $C_1$-$C_9$ alkyl groups are lower alkyl groups such as methyl, ethyl, isopropyl, isobutyl, 1-methylpropyl, propyl, butyl, t-butyl, pentyl, isoamyl, neopentyl, hexyl, and further include heptyl, octyl, nonyl, 4-methylpentyl, 5-methylhexyl, 6-methylheptyl, 7-methyloctyl, etc.

Examples of phenyl-lower alkyl groups are benzyl, 1-phenylethyl, 2-phenylethyl, 3-phenylpropyl, 4-phenylbutyl, 5-phenylpentyl, 6-phenylhexyl, etc.

Examples of cycloalkyl groups are cycloalkyl groups having 3 to 8 carbon atoms such as cyclopropyl, cyclobutyl, cyclopentyl, cyclohexyl, cycloheptyl, cyclooctyl, etc.

Examples of alkylene groups R in

represented by $R_5R_6N$- are straight chain alkylene groups having 3 to 8 carbon atoms such as trimethylene, tetramethylene, pentamethylene, hexamethylene, octamethylene, etc.

Examples of

moiety in the group

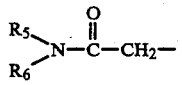

are amino, methylamino, ethylamino, propylamino, isopropylamino, butylamino, isobutylamino, 1-methylpropylamino, t-butylamino, pentylamino, isoamylamino, neopentylamino, hexylamino, phenylamino, benzylamino, phenethylamino, N,N-dimethylamino, N,N-dipropylamino, N,N-dipentylamino, N-phenyl-N-methylamino, N-phenyl-N-ethylamino, N-phenyl-N-propylamino, N-phenyl-N-benzylamino, N,N-diphenylamino, N-benzyl-N-methylamino, N-benzyl-N-isopropylamino, N,N-dibenzylamino, α-naphthylamino, β-naphthylamino, cyclopropylamino, cyclobutylamino, cyclopentylamino, cyclohexylamino, cyclooctylamino, N-cyclopentyl-N-methylamino, N-cyclohexyl-N-ethylamino, N-cyclopentyl-N-phenylamino, N,N-dicyclopentylamino, etc.

Examples of

moiety are aziridino, azetidino, pyrrolidino, piperidino, hexahydroazepino, octahydroazocino, etc.

Examples of $C_2$–$C_4$ alkylene groups formed by $R_7$ and $R_8$ taken together are ethylene, trimethylene, tetramethylene, etc.

Examples of groups

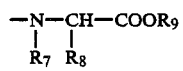

are residues of amino acid such as glycine, L-alanine, L-valine, L-leucine, L-isoleucine, L-phenylalanine, L-proline, D-alanine, D-valine, D-leucine, D-isoleucine, D-phenylalanine, D-proline, (S)-2-azetidine-carboxylic acid, L-pipecolic acid and the like or residues of amino acid lower alkyl ester such as glycine methyl ester, L-alanine methyl ester, L-valine ethyl ester, L-leucine methyl ester, L-isoleucine methyl ester, L-phenylalanine methyl ester, L-proline methyl ester and the like.

With respect to the substituents in the substituted lower alkoxy groups represented by $R_4$, examples of lower alkoxycarbonyl groups are groups formed by linking the lower alkoxy group having 1 to 6 carbon atoms to a carbonyl group, such as methoxycarbonyl, ethoxycarbonyl, propoxycarbonyl, isopropoxycarbonyl, butoxycarbonyl, isobutoxycarbonyl, 1-methylpropoxycarbonyl, t-butoxycarbonyl, pentyloxycarbonyl, isoamyloxycarbonyl, neopentyloxycarbonyl, hexyloxycarbonyl, etc. Representative of halogen atoms are fluorine, chlorine, bromine, iodine, etc. Illustrative of arylcarbamoyl groups are monophenylcarbamoyl, N,N-diphenylcarbamoyl, α-naphthylcarbamoyl, β-naphthylcarbamoyl, etc. Examples of pyridyl groups are 2-pyridyl, 3-pyridyl and 4-pyridyl. Representative of lower alkoxycarbonylamino groups are methoxycarbonylamino, ethoxycarbonylamino, propoxycarbonylamino, butoxycarbonylamino, t-butoxycarbonylamino, pentyloxycarbonylamino, hexyloxycarbonylamino, etc.

Examples of the substituted lower alkoxy groups represented by $R_4$ and substituted with lower alkoxy, lower alkoxy-carbonyl, halogen, carbamoyl, arylcarbamoyl, pyridyl, a group

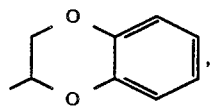

4-(1,1-diphenylmethyl)-1-piperazinyl or lower alkoxycarbonylamino are lower alkoxy groups having 1 to 6 carbon atoms and substituted with one member selected from the group consisting of lower alkoxy, lower alkoxycarbonyl, carbamoyl, arylcarbamoyl, pyridyl, a group

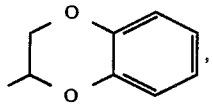

4-(1,1-diphenylmethyl)-1-piperazinyl and lower alkoxycarbonylamino, or lower alkoxy groups substituted with 1 to 3 halogen atoms. Specific examples thereof are methoxyethoxy, methoxypropoxy, methoxypentyloxy, methoxyhexyloxy, ethoxymethoxy, t-butoxymethoxy, hexyloxyethoxy, methoxycarbonylmethoxy, 1-methoxycarbonylethoxy, 2-methoxycarbonylethoxy, 6-ethoxycarbonylhexyloxy, 2-chloroethoxy, 2-bromoethoxy, 2,2-dichloroethoxy, 2,2,2-trichloroethoxy, 2,2,2-trifluoroethoxy, 6-fluorohexyloxy, carbamoylmethyloxy, 2-carbamoylethyloxy, 3-carbamoylpropyloxy, phenylcarbamoylmethyloxy, N,N-diphenylcarbamoylmethyloxy, 2-phenylcarbamoylethyloxy, 2-picolyloxy, 3-picolyloxy, 4-picolyloxy, 1,4-benzodioxan-2-ylmethyloxy, 2-(1,4-benzodioxan-2-yl)ethyloxy, 2-[4-(1,1-diphenylmethyl)-1-piprazinyl]ethyloxy, 4-[4-(1,1-diphenylmethyl)-1-piperazinyl]butyloxy, 2-t-butoxycarbonylaminopropoxy, 2-t-butoxycarbonylaminoethoxy, 2-methoxycarbonylaminopropoxy, etc.

Representative of aryloxy groups are phenyloxy, α-naphthyloxy, β-naphthyloxy, etc.

Examples of tocopheryloxy groups are α-tocopheryloxy, β-tocopheryloxy, γ-tocopheryloxy and δ-tocopheryloxy.

Illustrative of 1-(aryl-lower alkyl)-piperidyloxy groups are 1-phenylmethyl-3-piperidyloxy, 1-phenylmethyl-2-piperidyloxy, 1-phenylmethyl-4-piperidyloxy, 1-(1-phenethyl)-3-piperidyloxy, 1-(2-phenethyl)-3-piperidyloxy, 1-(2-phenethyl)-4-piperidyloxy, 1-(3-phenylpropyl)-3-piperidyloxy, 1-(3-phenylpropyl)-4-piperidyloxy, 1-(6-phenylhexyl)-3-piperidyloxy, etc.

Typical of lower alkoxycarbonyl-substituted arylamino groups are 2-methoxycarbonylphenylamino, 3-methoxycarbonylphenylamino, 4-methoxycarbonylphenylamino, 2-ethoxycarbonylphenylamino, 3-ethoxycarbonylphenylamino, 4-ethoxycarbonylphenylamino, 2-propyloxycarbonylphenylamino, 2-butoxycarbonylphenylamino, 2-pentyloxycarbonylphenylamino, 2-hexyloxycarbonylphenylamino, 4-isopropyloxycarbonylphenylamino, 3-isobutyloxycarbonylphenylamino, etc.

Representative of lower alkylsulfonylamino groups are methanesulfonylamino, ethanesulfonylamino, etc.

Illustrative of arylsulfonylamino groups are phenylsulfonylamino, p-toluenesulfonylamino, α-naphthylsulfonylamino, β-naphthylsulfonylamino, etc.

The compounds of the formula (1) have asymmetric carbon atoms in the molecule and therefore optical isomers exist. The present invention includes all the isomers of the compounds.

The proline derivatives of the invention and salts thereof have an angiotensin converting enzyme-inhibitory activity and are useful for diagnosing, preventing and treating hypertension. The derivatives of the invention exhibit sustained effects, and are unlikely to cause kidney disorders and of low toxicity. Further the derivatives of the invention and salts thereof have an immunity-enhancing effect, expectorant activity, activity of reducing the intraocular pressure and activity of reducing lipid level, and therefore can be used as an immunostimulant, expectorant, agent for treating glaucoma, or agent for treating hyperlipemia.

The salts of the proline derivatives of the invention include pharmaceutically acceptable acid addition salts. Examples of acidic compounds useful for forming the acid addition salts are inorganic acids such as hydrochloric acid, sulfuric acid, nitric acid, phosphoric acid, hydrobromic acid and the like, and organic acids such as maleic acid, fumaric acid, malic acid, tartaric acid, citric acid, benzoic acid, benzenesulfonic acid, methanesulfonic acid and the like.

Of the proline derivatives of the invention, those having one or more acidic groups can be converted into salts by being acted on by a pharmaceutically acceptable base. The invention includes such salts. Examples of bases useful for forming such salts in the invention are inorganic bases such as sodium hydroxide, potassium hydroxide, calcium hydroxide, sodium carbonate, potassium hydrogencarbonate and the like and organic bases such as lysine, arginine, ornithine, morpholine, piperazine, piperidine, ethylamine, dimethylamine, triethylamine, dicyclohexylamine and the like.

A class of proline derivatives of the formula (1) according to this invention are compounds represented by the formula

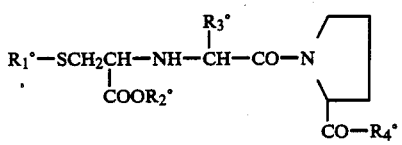

(1-1)

wherein $R_1°$ is adamantyl, benzocycloalkyl or cycloalkyl optionally substituted with lower alkyl, $R_2°$ is hydrogen or lower alkyl, $R_3°$ is lower alkyl and $R_4°$ is hydroxy or lower alkoxy.

Another class of proline derivatives of the invention are compounds represented by the formula

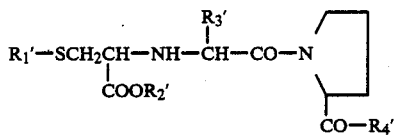

(1-2)

wherein $R_1'$ is a group

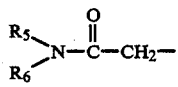

(wherein $R_5$ and $R_6$ are as defined above), $R_2'$ is hydrogen or lower alkyl, $R_3'$ is lower alkyl and $R_4'$ is hydroxy or lower alkoxy.

A further class of proline derivatives of the invention are compounds represented by the formula

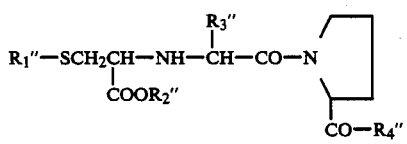

(1-3)

wherein $R_1''$ is $C_4$-$C_8$ alkyl, $R_2''$ is hydrogen or lower alkyl, $R_3''$ is lower alkyl and $R_4''$ is a group

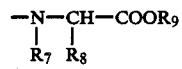

(wherein $R_7$, $R_8$ and $R_9$ are as defined above).

A still further class of proline derivatives of the invention are compounds represented by the formula

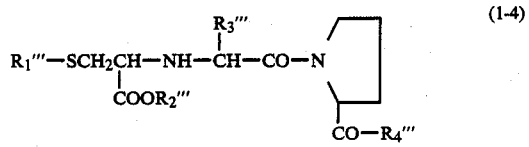

(1-4)

wherein $R_1'''$ is $C_1$-$C_9$ alkyl, $R_2'''$ is hydrogen or lower alkyl, $R_3'''$ is lower alkyl, $R_4'''$ is substituted lower alkoxy wherein the substituent is selected from the group consisting of lower alkoxy, lower alkoxycarbonyl, halogen, carbamoyl, arylcarbamoyl, pyridyl, a group <Reaction Scheme 1>

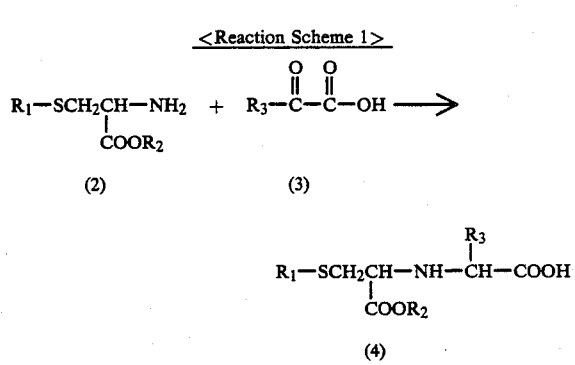

4-(1,1-diphenylmethyl)-1-piperazinyl and lower alkoxycarbonylamino, or $R_4'''$ is aryloxy, tocopheryloxy, 1-(aryl-lower alkyl)-piperidyloxy, amino, lower alkoxycarbonyl-substituted arylamino, lower alkyl-sulfonylamino or arylsulfonylamino.

Of the proline derivatives of the formula (1), preferred compounds are those wherein $R_1$ is cyclopentyl, 2-indanyl or n-heptyl, $R_2$ is ethyl, $R_3$ is methyl, $R_4$ is methoxy, residue of L-phenylalanine, residue of L-phenylalanine methyl ester, 1-phenylmethyl-3-piperidyloxy, methoxycarbonylmethoxy or 2-methoxyethoxy, with the proviso that $R_4$ is not methoxy when $R_1$ is n-heptyl.

The proline derivatives of the formula (1) according to the invention can be prepared by various processes, for example, those as described below in Reaction Schemes, which also indicate processes for producing intermediates for synthesizing the proline derivatives of the formula (1).

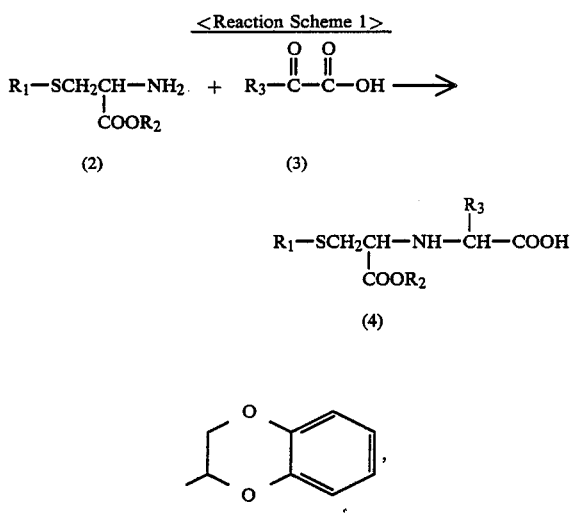

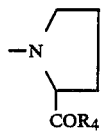

In the foregoing formulas, $R_1$, $R_2$ and $R_3$ are as defined in the formula (1).

According to the process as shown in Reaction Scheme 1, the cysteine derivative (2) is treated with the α-keto acid (3) to give the compound (4). This reaction is a reductive bond-forming reaction using complex metal hydrides, and can be conducted by reducing the Schiff base formed by the reaction of the cysteine derivative (2) with the α-keto acid (3). Examples of complex metal hydrides are sodium borohydride, lithium borohydride, sodium cyanoborohydride, lithium cyanoborohydride and the like. The complex is used in an amount of about 2 to about 6 moles, preferably about 2 to about 3 moles, per mole of the cysteine derivative (2). The amount of α-keto acid used is about 1 to about 10 moles, preferably about 3 to about 5 moles, per mole of the cysteine derivative (2). The reaction is carried out in an inert solvent which does not adversely affect the reaction. Examples of useful solvents are water; alcohols such as ethanol, methanol, 2-propanol and the like; ethers such as diethyl ether, tetrahydrofuran (THF), dioxane and the like; and aprotic polar solvents such as dimethylformamide (DMF), dimethylsulfoxide (DMSO) and the like. The reaction is conducted usually at 0° to 50° C., preferably at or around room temperature and is completed in about 3 to about 24 hours. When using sodium cyanoborohydride or lithium cyanoborohydride, the reaction rapidly proceeds at about pH 6.5 to about pH 8.5, preferably around a neutral pH range.

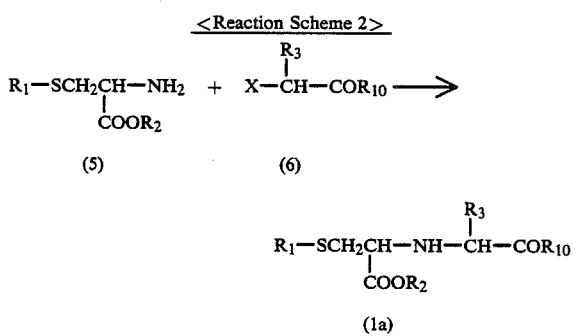

In the foregoing formulas, $R_1$, $R_2$ and $R_3$ are as defined in the formula (1), $R_{10}$ is hydroxyl, lower alkoxy, a group

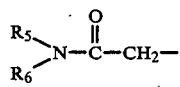

(wherein $R_4$ is as defined in the formula (1)), diphenylmethyloxy, phthalimidomethyloxy or p-methoxybenzyloxy, and X is halogen, alkylsulfonyloxy, or arylsulfonyloxy.

Representative of halogen atoms represented by X in the compound (6) are chlorine, bromine, iodine and the like. Illustrative of alkylsulfonyloxy groups in the compound (6) are lower alkylsulfonyloxy groups such as methanesulfonyloxy and ethanesulfonyloxy, and trifluoromethanesulfonyloxy and the like. Typical of arylsulfonyloxy groups in the compound (6) are p-toluenesulfonyloxy, benzenesulfonyloxy, p-chlorobenezenesulfonyloxy, mesitylenesulfonyloxy and the like.

According to the process shown in Reaction Scheme 2, the cysteine derivative (5) is alkylated with the compound (6) to give the compound (1a). The alkylation reaction is conducted in a suitable solvent in the presence of an acid binder. Examples of useful solvents are alcohols such as methanol, ethanol, 2-propanol, t-butanol and the like; ethers such as diethyl ether, tetrahydrofuran (THF), dioxane and the like; and aprotic polar solvents such as dimethylformamide (DMF), dimethylsulfoxide (DMSO), hexamethylphosphoric triamide (HMPA) and the like. Examples of useful acid binders are alkali metal carbonates such as sodium carbonate, potassium carbonate and the like, and alkali metal hydrogencarbonate such as sodium hydrogencarbonate, potassium hydrogencarbonate and the like; organic tertiary amines such as triethylamine, pyridine, 1,8-diazabicyclo-[5,4,0]undecane-7-ene (DBU) and the like. The acid binder is used in an amount of about 1 to about 2 moles, preferably about 1 to about 1.2 moles, per mole of the cysteine derivative (5). The compound (6) is usually used in an amount of at least about 1 mole, preferably about 1 to about 1.2 moles, per mole of the cysteine derivative (5). The reaction is conducted usually at about 0° to about 80° C., preferably at or around room temperature and is completed in about 3 to about 72 hours.

The cysteine derivative (5) wherein $R_1$ is a group $$\begin{array}{c} R_5 \\ \phantom{R_5} \diagdown \\ \phantom{R_5R_5} N-\overset{O}{\overset{\|}{C}}-CH_2- \\ \phantom{R_5} \diagup \\ R_6 \end{array}$$

(wherein $R_5$ and $R_6$ are as defined in the formula (1)) which is used as one of the starting materials in the reaction can be synthesized in accordance with the processes disclosed, for example, in M. Verderame, J. Pharm. Sci., 50, 312 (1961), etc. The cysteine derivatives (5) wherein $R_1$ is $C_1$-$C_9$ alkyl, adamantyl, benzocycloalkyl or cycloalkyl optionally substituted with lower alkyl can be synthesized in accordance with the processes described, for example, in J. Org. Chem., 16, 749 (1959); Helv. Chim. Acta., 32, 866 (1949); Chem.

Pharm. Bull., 26(5), 1576 (1978); Arch. Pharm. (Weinheim) 316, 934 (1983), etc.

The compounds (6) wherein $R_{10}$ is hydroxyl or lower alkoxy which are used as the other starting material in the reaction are known or can be easily synthesized by conventional processes. The compounds (6) wherein $R_{10}$ is a group

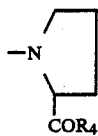

(wherein $R_4$ is as defined in the formula (1)) can be synthesized according to the process to be described below in Reaction Scheme 7.

<Reaction Scheme 3>

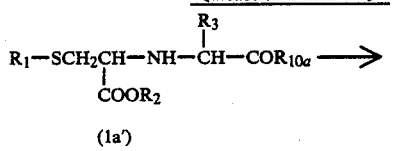

(1a')

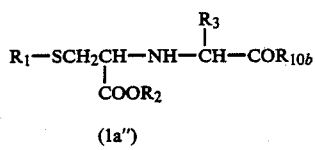

(1a'')

In the foregoing formulas, $R_1$, $R_2$ and $R_3$ are as defined in the formula (1), $R_{10a}$ is t-butoxy, a group

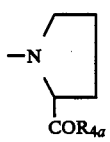

(wherein $R_{4a}$ is t-butoxy, p-methoxybenzyloxy, diphenylmethyloxy, phthalimidomethyloxy or a group

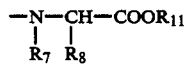

(wherein $R_7$ and $R_8$ are as defined in the formula (1) and $R_{11}$ is t-butyl), p-methoxybenzyloxy, diphenylmethyloxy or phthalimidomethyloxy, $R_{10b}$ is hydroxyl or a group

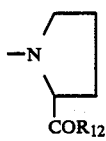

wherein $R_{12}$ is hydroxyl or a group

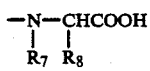

(wherein $R_7$ and $R_8$ are as defined above).

According to the process shown in Reaction Scheme 3, the compound (1a'') can be prepared by treating the compound (1a') with an acid in the presence or absence of a scavenger, preferably in the presence of a scavenger such as anisole, thioanisole, dimethylsulfide and the like.

Examples of acids useful in the acid treatment are trifluoroacetic acid (TFA), methanesulfonic acid, trifluoromethanesulfonic acid, hydrochloric acid, hydrobromic acid, hydrofluoric acid, acetic acid and the like. The reaction can be performed in the absence or in the presence of a solvent which does not adversely affect the reaction. Suitable examples of the solvents are ethers such as diethyl ether, THF, dioxane and the like; esters such as methyl acetate, ethyl acetate and the like; and halogenated hydrocarbons such as methylene chloride, chloroform and the like. The scavenger such as anisole and the like is used in an amount of usually about 1 to 10 moles, preferably about 3 to about 5 moles, per mole of the compound (1a'). The reaction is conducted at about 0° to about 50° C., preferably about 0° to about 25° C. and is completed in about 30 minutes to about 10 hours.

<Reaction Scheme 4>

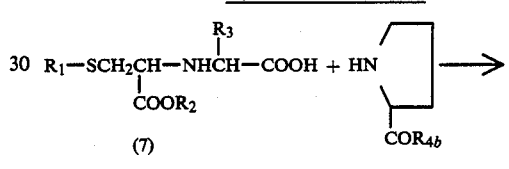

(7) (8)

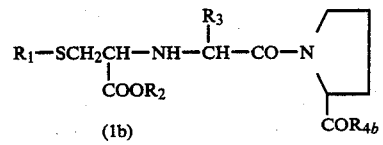

(1b)

In the foregoing formulas, $R_1$, $R_2$ and $R_3$ are as defined in the formula (1), and $R_{4b}$ is lower alkoxy, a group

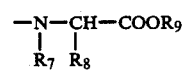

(wherein $R_7$, $R_8$ and $R_9$ are as defined in the formula (1)) or substituted lower alkoxy wherein the substituent is selected from the group consisting of lower alkoxy, lower alkoxycarbonyl, halogen, carbamoyl, arylcarbamoyl, pyridyl, a group

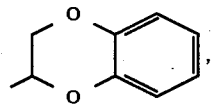

4-(1,1-diphenylmethyl)-1-piperazinyl and lower alkoxycarbonylamino, or $R_{4b}$ is aryloxy, tocopheryloxy, 1-(aryl-lower alkyl)-piperidyloxy, amino, lower alkoxycarbonyl-substituted arylamino, lower alkylsulfonylamino or arylsulfonylamino, with the proviso that $R_{4b}$ is not lower alkoxy when $R_1$ is $C_1$-$C_9$ alkyl.

According to Reaction Scheme 4, the compound (1b) of this invention can be produced by reacting the carboxylic acid (7) obtained in Reaction Schemes 1 to 3 with the amine (8). The reaction can be conducted by various processes according to amide bond-forming reaction, for example, as stated below.

(a) A condensation reaction in which the carboxylic acid (7) is condensed with the amine (8) in the presence of a condensing agent.

(b) A mixed acid anhydride method in which the carboxylic acid (7) is treated with an alkyl haloformate to obtain a mixed anhydride with which the amine (8) is allowed to react.

(c) An activated ester method in which the carboxylic acid (7) is made into an active ester such as p-nitrophenyl ester, N-hydroxysuccinimide ester, N-hydroxy-5-norbornene-2,3-dicarboximide ester or the like which is then treated with the amine (8).

(d) A carboxylic acid halide method in which the halide of the carboxylic acid (7) is reacted with the amine (8).

(e) Other processes

For example, the carboxylic acid (7) is treated with a dehydrating agent such as acetic anhydride to obtain an acid anhydride with which the amine (8) is allowed to react. It is also possible as another option to treat the amine (8), at a high temperature and under a high pressure, with an ester of the carboxylic acid (7) formed by use of lower alcohol.

The processes described above in (a) to (e) can be carried out under substantially the same conditions as in conventional respective processes. Of the foregoing processes, the process (a) is preferred and hereinafter described in detail. The process (a) employs a condensing agent such as N,N'-dicyclohexylcarbodiimide (DCC), DCC-N-hydroxysuccinimide (HOSu), DCC-N-hydroxybenzotriazole (HOBt), DCC-N-hydroxy-5-norbornene-2,3-dicarboximide (HONB), diphenylphosphorylazide (DPPA)-triethylamine, diethylphosphorocyanidate (DEPC)-triethylamine, water-soluble carbodiime.HCl (WSCD.HCl)-HOBt, etc. The reaction is conducted generally in a suitable solvent. Useful solvents can be any of various conventional solvents which do not adversely affect the reaction. Examples of suitable solvents are halogenated hydrocarbons such as methylene chloride, chloroform, dichloroethane and the like; aromatic hydrocarbons such as benzene, toluene, xylene and the like; ethers such as diethyl ether, THF, dioxane and the like; esters such as methyl acetate, ethyl acetate and the like; and aprotic polar solvents such as DMF, DMSO, HMPA and the like. The amount of the amine (8) used is usually at least about 1 mole, preferably about 1 to about 1.2 moles, per mole of the carboxylic acid (7). The condensing agent is used in an amount of about 1 to about 2 moles, preferably about 1 to about 1.2 moles, per mole of the carboxylic acid (7). The reaction is conducted at generally about −20° to about 30° C., preferably about −10° C. to room temperature, and is completed in about 3 to about 24 hours.

The amines (8) wherein $R_{4b}$ is lower alkoxy or amino which are used as one of the starting compounds in the reaction of Reaction Scheme 4 are known compounds. The amine (8) wherein $R_{4b}$ is a group

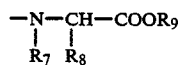

(wherein $R_7$, $R_8$ and $R_9$ are as defined in the formula (1)) can be easily prepared by various conventional processes such as those commonly used for synthesis of peptides and those disclosed in literature, e.g. M. Bodanszky, Y. S. Klausner, M. A. Ondetti: "Peptide Synthesis", 2nd edition (1976) and "Seikagaku Jikken Koza", vol. 1, Chemistry of Protein IV, edited by The Japanese Biochemical Society and published by Tokyo Kagaku Dojin (1977) as well as the processes shown in Reaction Schemes 5B and 6 to follow. The other amines (8) can be synthesized by the processes of Reaction Schemes shown below <Reaction Scheme 5A>

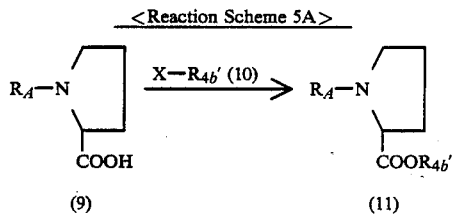

In the foregoing formulas, $R_A$ is benzyloxycarbonyl, p-methoxybenzyloxycarbonyl, t-butoxycarbonyl or t-amyloxycarbonyl, X is halogen, alkylsulfonyloxy or arylsulfonyloxy, and $R_{4b}'$ is substituted lower alkyl wherein the substituent is selected from the group consisting of lower alkoxy, lower alkoxycarbonyl, halogen, carbamoyl, arylcarbamoyl, pyridyl, a group

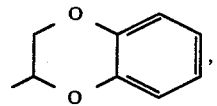

4-(1,1-diphenyl-methyl)-1-piperazinyl and lower alkoxycarbonylamino, or $R_{4b}'$ is 1-(aryl-lower alkyl)-piperidyl.

Representative of halogen atoms represented by X in the compound (10) are chlorine, bromine, iodine and the like. Illustrative of alkylsulfonyloxy groups are lower alkylsulfonyloxy such as methanesulfonyloxy, ethanesulfonyloxy and the like. Typical of arylsulfonyloxy groups are p-toluenesulfonyloxy, benzenesulfonyloxy, p-chlorobenzenesulfonyloxy, mesitylenesulfonyloxy and the like.

According to the process shown in Reaction Scheme 5A, the carboxylic acid (9) is alkylated with the compound (10), whereby the compound (11) is prepared. The alkylation reaction is conducted in a suitable solvent in the presence of a base. Examples of useful solvents are alcohols such as methanol, ethanol, 2-propanol, t-butanol and the like; ethers such as diethyl ether, tetrahydrofuran (THF), dioxane and the like; and aprotic polar solvents such as dimethylformamide (DMF), dimethylsulfoxide (DMSO), hexamethylphosphoric triamide (HMPA) and the like. Examples of useful bases are alkali metal carbonates such as sodium carbonate, potassium carbonate and alkali metal hydrogencarbonate such as sodium hydrogencarbonate, potassium hydrogencarbonate and the like; and organic tertiary amines such as triethylamine, pyridine, 1,8-diazabicyclo[5,4,0]undecane-7-ene (DBU) and the like. The base is used in an amount of about 1 to about 2 moles, preferably about 1 to about 1.2 moles, per mole of the carboxylic acid (9). The amount of the compound (10) used is generally at least about 1 mole, preferably about 1 to about 1.2 moles, per mole of the compound (9). The reaction is conducted usually at 10° to 100° C. preferably at or around room temperature and is completed in about 8 to about 48 hours.

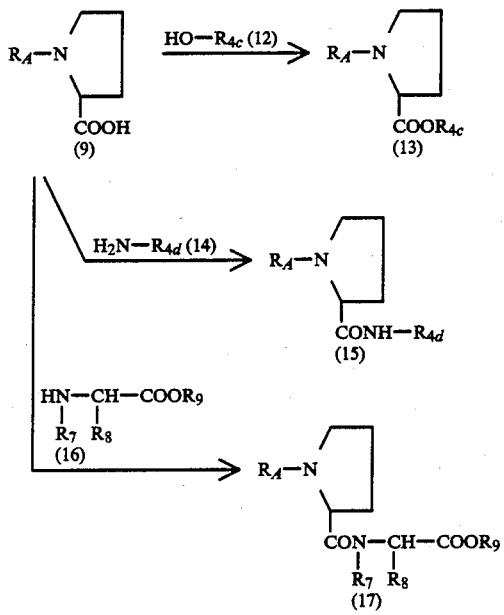

In the foregoing formulas, $R_A$ is as defined above, $R_{4c}$ is aryl, tocopheryl or $R_{4b}'$, $R_{4d}$ is lower alkoxycarbonyl-substituted aryl, lower alkylsulfonyl or arylsulfonyl, and $R_7$, $R_8$ and $R_9$ are as defined in the formula (1).

According to the process shown in Reaction Scheme 5B, the carboxylic acid (9) is condensed with the compound (12), (14) or (16) to give the compound (13), (15) or (17), respectively. The condensation reaction can be carried out in accordance with the methods (a) through (e) described above with respect to Reaction Scheme 4. Alternatively, the compounds (13), (15) and (17) can also be produced in high yields by using DCC or WSCD.HCl in the presence of a catalytic amount of 4-dimethylaminopyridine (4DMAP) or 4-pyrrolidinopyridine. The reaction is conducted in a suitable solvent. Useful solvents can be any of those known in the art which do not adversely affect the reaction. Examples of suitable solvents are halogenated hydrocarbons such as methylene chloride, chloroform, dichloroethane and the like; aromatic hydrocarbons such as benzene, toluene, xylene and the like; ethers such as diethyl ether, THF, dioxane and the like; esters such as methyl acetate, ethyl acetate and the like; and aprotic polar solvents such as DMF, DMSO, HMPA and the like. The amounts of the compounds (12), (14) and (16) used are each at least about 1 mole, preferably about 1 to about 1.2 moles, per mole of the carboxylic acid (9). The condensing agent is used in an amount of about 1 to about 2 moles, preferably about 1 to about 1.2 moles, per mole of the carboxylic acid (9). The reaction is conducted usually at −10° to 30° C., preferably about 0° C. to room temperature and is completed in about 5 to about 24 hours.

<Reaction Scheme 6>

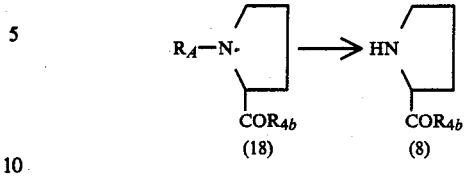

In the foregoing formulas, $R_A$ and $R_{4b}$ are as defined above.

According to the process shown in Reaction Scheme 6, the amino-protecting group $R_A$ is removed by catalytic reduction or acid treatment from the compound (18) obtained in Reaction Schemes 5A and 5B, giving the amine (8).

When $R_A$ is benzyloxycarbonyl or p-methoxybenzyloxycarbonyl, the amine (8) can be easily obtained by the catalytic hydrogenation. The reduction is effected by usual catalytic process in which hydrogenation is conducted using a catalyst conventionally employed such as platinum oxide, palladium-carbon, palladium black and the like. The amount of the catalyst used is not specifically limited and is widely variable. It is usually about 5 to about 10% by weight of the compound (18). The hydrogenation using the catalyst is performed in a solvent, such as water; lower alcohols such as methanol, ethanol and the like; ethers such as diethyl ether, tetrahydrofuran, dioxane and the like; aprotic polar solvents such as dimethylformamide, dimethylacetamide and the like, and mixtures of such solvents. The hydrogenation is carried out at a hydrogen pressure of, for example, 1 atm. and at a temperature of about 0° to about 40° C. and is completed in about 30 minutes to about 6 hours.

When $R_A$ is any of benzyloxycarbonyl, p-methoxybenzyloxycarbonyl, t-butoxycarbonyl and t-amyloxycarbonyl, the amine (8) can be easily produced by the acid treatment. The compound (18) is treated with an acid in the absence or presence of a scavenger such as anisole, thioanisole, dimethylsulfide and the like, thereby giving the amine (8) without producing any by-product.

Examples of acids useful in the acid treatment are trifluoracetic acid (TFA), methanesulfonic acid, trifluoromethanesulfonic acid, hydrochloric acid, hydrobromic acid, hydrofluoric acid, acetic acid and the like. The reaction can be performed in the absence or presence of a solvent, e.g. ethers such as diethyl ether, THF, dioxane and the like; esters such as methyl acetate, ethyl acetate and the like; and halogenated hydrocarbons such as methylene chloride, chloroform and the like. The scavenger such as anisole and the like is used in an amount of usually about 1 to 10 moles, preferably about 3 to about 5 moles, per mole of the compound (18). The reaction is conducted at about 0° to about 50° C., preferably about 0° to about 25° C. and is completed in about 30 minutes to about 10 hours.

<Reaction Scheme 7>

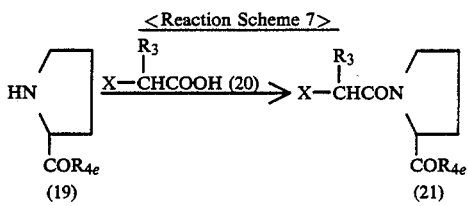

In the foregoing formulas, $R_{4e}$ is $R_{4b}$ or hydroxyl (i.e. $R_{4e}=R_4$), and X and $R_3$ are as defined above.

According to the process shown in Reaction Scheme 7, the carboxylic acid (20) is condensed with the amine (8) prepared in Reaction Scheme 6 or proline, i.e., amine (19) to give the compound (21). The condensation reaction can be carried out in the same manner as in Reaction Scheme 4.

<Reaction Scheme 8>

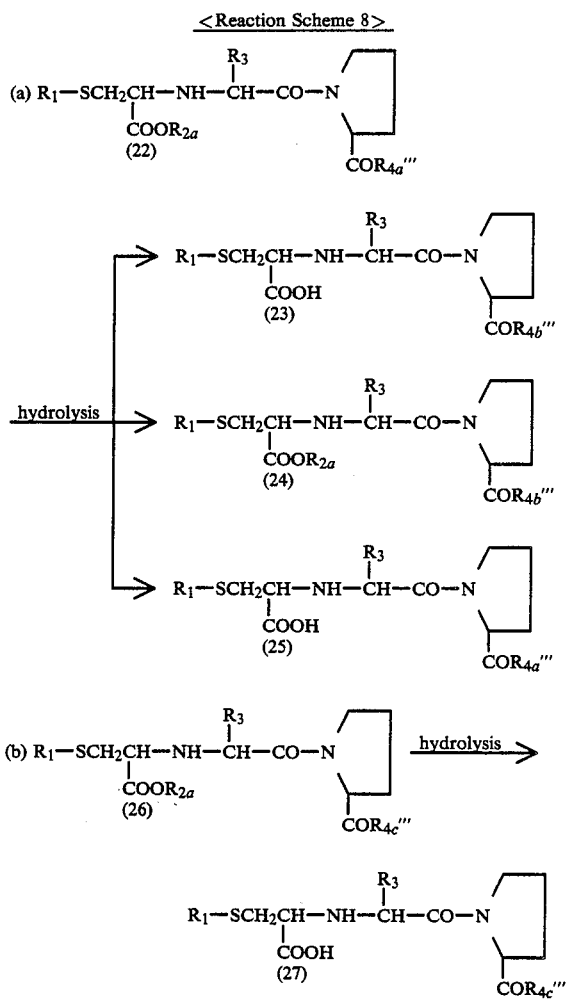

In the foregoing formulas, $R_1$ and $R_3$ are as defined above, $R_{2a}$ is lower alkyl and $R_{4a}'''$ is lower alkoxy, a group

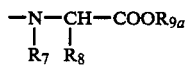

(wherein $R_7$ and $R_8$ are as defined above and $R_{9a}$ is lower alkyl), or substituted lower alkoxy wherein the substitutent is selected from the group consisting of lower alkoxy, lower alkoxycarbonyl, halogen, carbamoyl, arylcarbamoyl, pyridyl, a group

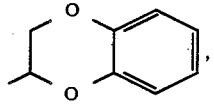

4-(1,1-diphenylmethyl)-1-piperazinyl and lower alkoxycarbonylamino, or $R_{4a}'''$ is aryloxy, tocopheryloxy, 1-(aryl-lower alkyl)-piperidyloxy or lower alkoxycarbonyl-substituted arylamino, $R_{4b}'''$ is hydroxy or a group

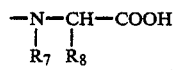

(wherein $R_7$ and $R_8$ are as defined above) or carboxy-substituted arylamino, and $R_{4c}'''$ is amino, lower alkylsulfonylamino or arylsulfonylamino.

According to the processes as shown in Reaction Scheme 8-a) or b), the compound (22) or (26) is hydrolyzed in the presence of a basic compound to give the compound (23), (24), (25) or (27). The hydrolysis is conducted in water or in a mixture of water and an organic solvent. Examples of the solvents are lower alcohols such as methanol, ethanol and the like; ethers such as diethyl ether, THF, dioxane and the like; acetonitrile, etc. Examples of the basic compounds are alkali metal hydroxides such as sodium hydroxide, potassium hydroxide, lithium hydroxide, etc.

In the hydrolysis under Reaction Scheme 8-(a), proportions of the products formed vary depending on the reaction temperature, reaction time and amount of the basic compound, especially on the amount of the basic compound. Specifically, if the amount of the basic compound is about 2.5 to about 4 moles per mole of the compound (22), only the compound (23) will be formed selectively. On the other hand, if the amount of the basic compound is about 1 to about 1.5 moles per mole of the compound (22), the compounds (23), (24) and (25) are produced as a mixture.

In the hydrolysis under Reaction Scheme 8-(b), the basic compound is used in an amount of about 1.2 to about 2 moles per mole of the compound (26), whereby the compound (27) alone can be obtained in a high yield.

The foregoing hydrolysis reactions are usually conducted at a temperature of about 0° to about 40° C., preferably at room temperature, and are completed in about 1 to about 12 hours.

The compounds obtained in the reactions shown in Reaction Schemes 1 to 8 can be easily separated from the reaction mixture and purified by conventional separation methods including solvent extraction, dilution, distillation and recrystallization methods, column chromatography, preparative thin-layer chromatography, ion-exchange chromatography, etc.

For use as pharmaceuticals, the compound of this invention can be administered to humans as it is or as formulated into pharmaceutical compositions in combination with conventional pharmaceutically acceptable carriers. The dosage form of pharmaceutical compositions is not specifically limited but can be suitably determined according to a specific purpose. For oral compositions, tablets, powders, granules, solutions and the like are available. Parenteral preparations include injectable solutions and the like. The daily dose of the active component in the pharmaceutical composition is not specifically limited but can be suitable determined over a wide range. Generally it ranges from about 0.06 to about 50 mg/kg body weight/day, preferably about 0.06 to about 10 mg/kg body weight/day, in order to achieve the contemplated result. About 1 to about 500 mg of the active component is used per dosage unit.

The oral preparations can be prepared in the form of capsules, solutions or the like by conventional methods. For the preparation of tablets, the compound of the invention is mixed with a pharmaceutically acceptable excipient such as gelatin, starch, lactose, magnesium stearate, talc, gum arabic and the like. For the preparation of capsules, the compound of the invention is mixed with a pharmaceuticall acceptable inert filler or diluent and the mixture is dividedly placed in hard gelatin or soft gelatin capsules or the like. Syrups or elixirs can be prepared by mixing the compound of the invention with sweetening such as saccharose, antiseptic such as methyl- or propyl-paraben, coloring agent, flavoring or the like. Parenteral preparations can be prepared by conventional methods. For their preparation, the compound of the invention is dissolved in a sterilized liquid carrier. Preferred carriers are water and physiological saline. Liquid preparations having the desired transparency, stability and suitability for parenteral administration can be prepared by dissolving about 1 to about 500 mg of active component in water and an organic solvent and also in polyethylene glycol having a molecular weight of about 200 to about 5000. Preferably such liquid preparations contain a lubricant such as sodium carboxymethyl cellulose, methyl cellulose, polyvinyl pyrrolidone, polyvinyl alcohol, etc. The liquid preparations may further have incorporated therein a bactericide and fungicide such as benzyl alcohol, phenol, thimerosal and the like, saccharose, sodium chloride and like isotonic agent, stabilizer, buffer, etc. To improve the stability, parenteral preparations filled into containers are lyophilized for removal of water by methods known in the art. The lyophilized powder can be reconstituted before use.

This invention will be described below in greater detail with reference to the following examples for preparation of the compounds of the invention and reference examples for preparation of starting materials useful for production of the compounds of the invention.

In Examples 1 to 8 and Reference Examples 1 to 12, the terms "α-isomer" and "β-isomer" are used to mean the following.

Of the two isomers produced as the reaction products of the cysteine derivative (5)of Reaction Scheme 2 (wherein $R_1$ is adamantyl, benzocycloalkyl or cycloalkyl optionally substituted with lower alkyl) and 2-bromopropionic acid t-butyl ester, a first eluate obtained in silica gel column chromatography (using ether/n-hexane) is hereinafter referred to as "α-isomer" and a second eluate therefrom as "β-isomer". Also the compounds derived from the α-isomer are called "α-isomers" and those from the β-isomer are called "β-isomers".

REFERENCE EXAMPLE 1

N-[(R)-1-ethoxycarbonyl-2-(1-adamantylthio)ethyl]-alanine t-butyl ester (α- and β-isomers)

A 10 g quantity of S-1-adamatyl-L-cysteine ethyl ester and 7.3 g of 2-bromopropionic acid t-butyl ester were dissolved in 30 ml of HMPA. To the solution was added 4.9 ml of triethylamine and the mixture was stirred at room temperature for 36 hours. The reaction mixture was poured into ice water and the mixture was extracted with ethyl acetate. The extract was fully washed with water and dried over anhydrous sodium sulfate. The solvent was evaporated off under reduced pressure and the residue was separated and purified by silica gel column chromatography (a 1:3 mixture of ether and n-hexane as an eluent), producing the α-isomer of the title compound as a colorless oil from the first eluate.

Yield 3.6 g.

$[\alpha]_D^{25} = +11.2°$ (c=1.3, ethanol)

NMR (CDCl$_3$): δ1.1-2.4 (22H, m), 1.45 (9H, s), 2.81 (2H, d, J=6 Hz), 3.40 (2H, q, J=7 Hz), 4.20 (2H, q, J=7 Hz)

The β-isomer of the tilte compound was obtained as a colorless oil from the second eluate. Yield 1.9 g.

$[\alpha]_D^{25} = -9.1°$ (c=0.3, ethanol)

NMR (CDCl$_3$): δ1.2-2.2 (22H, m), 1.47 (9H, s) 2.71 (1H, d—d, J=14 Hz, 8 Hz), 2.90 (1H, d—d, J=14 Hz, 6 Hz), 3.19 (1H, q, J=7 Hz), 3.43 (1H, d—d, J=6 Hz, 8 Hz), 4.21 (2H, q, J=7 Hz).

REFERENCE EXAMPLES 2 TO 7

The compounds as listed below in Table 1 were obtained by following the general procedure of Reference Example 1.

TABLE 1

$$R_1-S-CH_2\overset{(R)}{\underset{CO_2C_2H_5}{CH}}-NH-\overset{\overset{CH_3}{|}}{\underset{*}{CH}}-CO_2-C(CH_3)_3$$

| Ref. Ex. No. | $R_1$ | Isomer (*) | Optical Rotation (Solvent: ethanol) | NMR(CDCl$_3$): δ |
|---|---|---|---|---|
| 2 | 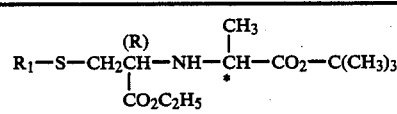 | α | $[\alpha]_D^{25} = +26.1°$ (c = 0.9) | 1.2-1.9 (17H, m), 1.29 (3H, s) 1.45 (9H, s), 2.3-2.5 (1H, brs), 2.76 (2H, d, J=5Hz), 3.33 (1H, d, J=5Hz), 3.49 (1H, q, J=6Hz), 4.20 (2H, q, J=7Hz) |

TABLE 1-continued $$R_1-S-CH_2\underset{CO_2C_2H_5}{\overset{(R)}{CH}}-NH-\underset{*}{\overset{CH_3}{CH}}-CO_2-C(CH_3)_3$$

| Ref. Ex. No. | R₁ | Isomer (*) | Optical Rotation (Solvent: ethanol) | NMR(CDCl₃): δ |
|---|---|---|---|---|
| 3 |  | β | $[\alpha]_D^{25} = -17.9°$ (c = 0.6) | 1.2–1.8 (17H, m), 1.30 (3H, s) 1.47 (9H, s), 2.08 (1H, s), 2.67 (1H, d-d, J=13Hz, 7Hz), 2.83 (1H, d-d, J=13Hz, 6Hz), 3.29 (1H, q, J=7Hz), 3.45 (1H, d-d, J=6Hz, 7Hz), 4.21 (2H, q, J=7Hz) |
| 4 | 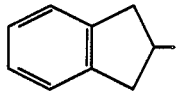 | α | $[\alpha]_D^{25} = +37.0°$ (c = 1.1) | 1.27 (3H, d, J=7Hz), 1.29 (3H, t, J=7Hz), 1.45 (9H, s), 2.0–2.1 (1H, brs), 2.8–3.9 (9H, m), 4.21 (2H, q, J=7Hz), 7.16 (4H, s) |
| 5 | 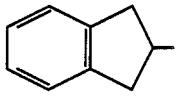 | β | $[\alpha]_D^{25} = -22.1°$ (c = 1.1) | 1.30 (3H, d, J=7Hz), 1.30 (3H, t, J=7Hz), 1.46 (9H, s), 2.16 (1H, brs), 2.7–3.9 (9H, m), 4.22 (2H, q, J=7Hz), 7.16 (4H, s) |
| 6 |  | α | $[\alpha]_D^{25} = +34.3°$ (c = 0.8) | 1.27 (3H, d, J=7Hz), 1.29 (3H, t, J=7Hz), 1.45 (9H, s), 1.5–2.2 (8H, m), 2.83 (2H, d, J=6Hz), 2.9–3.2 (1H, m), 3.32 (1H, q, J=7Hz), 3.47 (1H, t, J=7Hz), 4.20 (2H, q, J=7Hz) |
| 7 |  | β | $[\alpha]_D^{25} = -36.7°$ (c = 0.7) | 1.29 (3H, d, J=7Hz), 1.30 (3H, t, J=7Hz), 1.47 (9H, s), 1.5–2.1 (8H, m), 2.67 (1H, d-d, J=13Hz, 7.5Hz), 2.86 (1H, d-d, J=13Hz, 5.5Hz), 3.1–3.3 (1H, m), 3.30 (1H, q, J=7Hz), 3.44 (1H, q, J=7.5Hz, 5.5Hz), 4.21 (2H, q, J=7Hz) |

REFERENCE EXAMPLE 8

Preparation of N-[(R)-1-ethoxycarbonyl-2-(1-adamantylthio)ethyl]-alanine (β-isomer)

A 1.8 g portion of β-isomer of N-[(R)-1-ethoxycarbonyl-2-(1-adamanthythio)ethyl]-alanine t-butyl ester obtained in Reference Example 1 was dissolved in 25% HBr-acetic acid. The solution was stirred at room temperature for 2 hours. The solvent was evaporated off under reduced pressure and the residue was poured into ice water. The mixture was adjusted to a pH of 4 with a saturated aqueous solution of sodium hydrogen-carbonate. The solution was extracted with methylene chloride. The extract was washed with water and dried over anhydrous sodium sulfate. The solvent was distilled off under reduced pressure and the residue was crystallized from methylene chloride, giving the β-isomer of the title compound. Yield 1.2 g. M.p. 68°–72° C. $[\alpha]_D^{25} = +3.3°$ (c=0.7, ethanol)

REFERENCE EXAMPLES 9–12

The compounds as listed below in Table 2 were obtained by following the general procedure of Reference Example 8.

TABLE 2

$$R_1-S-CH_2\underset{CO_2C_2H_5}{\overset{(R)}{CH}}-NH-\underset{*}{\overset{CH_3}{CH}}-CO_2H$$

| Ref. Ex. No. | R₁ | Isomer (*) | Optical Rotation | Melting point (°C.) |
|---|---|---|---|---|
| 9 | 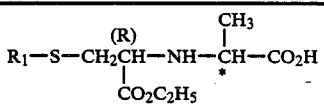 | β | $[\alpha]_D^{25} = -1.4°$ (c = 0.8, ethanol) | 125–129.5 |

TABLE 2-continued $$R_1-S-CH_2\overset{(R)}{\underset{CO_2C_2H_5}{CH}}-NH-\overset{CH_3}{\underset{*}{CH}}-CO_2H$$

| Ref. Ex. No. | $R_1$ | Isomer (*) | Optical Rotation | Melting point (°C.) |
|---|---|---|---|---|
| 10 | 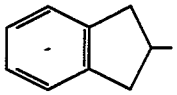 | β | $[\alpha]_D^{25} = +10.3°$ (c = 0.8, DMF) | 156–157 |
| 11 | 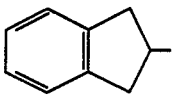 | α | $[\alpha]_D^{25} = +28.1°$ (c = 0.8, DMF) | 153–155 |
| 12 |  | β | $[\alpha]_D^{25} = -20.0°$ (c = 0.6, DMF) | 152–155 |

EXAMPLE 1

Preparation of N-[(R)-1-ethoxycarbonyl-2-(1-adamantylthio)ethyl]-alanyl-(S)-proline t-butyl ester (β-isomer)

A 830 mg portion of β-isomer of N-[(R)-1-ethoxycarbonyl-2-(1-adamantylthio)ethyl]-alanine obtained in Reference Example 6 and 390 mg of (S)-proline t-butyl ester were dissolved in 10 ml of DMF. To the solution were added with ice cooling and stirring 418 mg of WSCD HCl, 308 mg of N-hydroxybenzotriazole and 0.64 ml of triethylamine. The mixture was stirred with ice cooling for 2 hours and then further stirred at room temperature for 15 hours. The reaction mixture was poured into ice water and the mixture was dissolved in a saturated aqueous solution of sodium hydrogencarbonate to obtain a weakly alkaline solution. The solution was extracted with ethyl acetate. The extract was fully washed with water and dried over anhydrous sodium sulfate. The solvent was evaporated off under reduced pressure and the residue was purified by silica gel column chromatography (a 30:1 mixture of chloroform and methanol as an eluent), giving the β-isomer of the title compound as a colorless oil.

Yield 660 mg.

$[\alpha]_D^{25} = -64.9°$ (c=0.3, ethanol)

NMR (CDCl$_3$): δ1.29 (3H, t, J=7 Hz), 1.28 3H, d, J=6.5 Hz), 1.44, 1.46 (total 9H, each s), 1,6–2.2 (21H, m), 2.71 (1H, d—d, J=6 Hz, 13 Hz), 2.88 (1H, d—d, J=7 Hz, 13 Hz), 3.39 (1H, d—d, J=6 Hz, 7 Hz) 3.58 (1H, q, J=6.5 Hz), 4.20 (2H, q, J=7 Hz), 4.35–4.5 (1H, m).

EXAMPLE 2

Preparation of N-[(R)-1-ethoxycarbonyl-2-(1-methylcyclohexylthio)ethyl]-(S)-proline t-butyl ester (β-isomer)

Following the general procedure of Example 1, the title compound was prepared as a colorless oil from 2.0 g of N-[(R)-1-ethoxycarbonyl-2-(1-methylcyclohexylthio)ethyl]-alanine prepared in Reference Example 9. Yield 2.9 g.

$[\alpha]_D^{25} = -75.1°$ (c=0.7, ethanol).

NMR (CDCl$_3$): δ1.20 (3H, t, J=7 Hz), 1.28 (3H, s), 1.44, 1.46 (total 9H, each s), 1.2–2.4 (17H, m), 2.65 (1H, d—d, J=13 Hz, 7 Hz), 2.82 (1H, d—d, J=13 Hz, 6 Hz), 3.55 (1H, d—d, J=7 Hz), 3.5–3.8 (3H, m), 4.20 (2H, q, J=7 Hz), 4.3–4.6 (1H, m).

EXAMPLE 3

Preparation of N-[(R)-1-ethoxycarbonyl-2-(2-indanylthio)ethyl]-alanyl-(S)-proline t-butyl ester (β-isomer)

A 1.2 g portion of β-isomer of N-[(R)-1-ethoxycarbonyl-2-(2-indanylthio)ethyl]-alanine obtained in Reference Example 10, 670 mg of (S)-proline t-butyl ester and 710 mg of DEPC (90% content) were dissolved in 20 ml of DMF. To the solution was added dropwise a solution of 400 mg of triethylamine in 5 ml of DMF with ice cooling and stirring. The solution was stirred for 15 hours while being slowly returned to room temperature. Thereafter ice water was added to the reaction mixture and the mixture was made weakly alkaline with a saturated aqueous solution of sodium hydrogen-carbonate. The mixture was extracted with ethyl acetate. The extract was washed with water and then with a saturated aqueous solution of sodium chloride and dried over anhydrous sodium sulfate. The solvent was distilled off under reduced pressure. The residue was purified by silica gel column chromatography (a 30:1 mixture of chloroform and methanol as an eluent), giving the β-isomer of the title compound as a colorless oil.

Yield 1.7 g.

$[\alpha]_D^{25} = -69.7°$ (c=0.7, ethanol).

NMR (CDCl$_3$): δ1.29 (3H, t, J=7 Hz), 1.30 (3H, d, J=7 Hz), 1.44, 1.46 (total 9H, each s), 1.6–2.2 (4H, m), 2.29 (1H, brs), 2.7–3.8 (11H, m), 4.21 (2H, q, J=7 Hz), 4.4–4.5 (1H, m), 7.15 (4H, s).

EXAMPLE 4

Preparation of N-[(R)-1-ethoxycarbonyl-2-cyclopentylthioethyl]-alanyl-(S)-proline t-butyl ester (β-isomer)

Following the general procedure of Example 3, the β-isomer of the title compound was prepared as a colorless oil from 580 mg of the β-isomer of N-[(R)-1-ethoxycarbonyl-2-cyclopentylthioethyl]-alanine obtained in Reference Example 12. Yield 737 mg.

$[\alpha]_D^{26} = -88.1°$ (c=0.6, ethanol).

NMR (CDCl$_3$): δ1.29 (3H, t, J=7 Hz), 1.29 (3H, d, J=7 Hz), 1.44, 1.47 (total 9H, each s), 1.4–2.3 (12H, m), 2.65 (1H, d—d, J=13 Hz, 6 Hz), 2.86 (1H, d—d, J=13 Hz, 6 Hz), 3.0–3.3 (1H, m), 3.3–3.7 (4H, m), 4.20 (2H, q, J=7 Hz), 4.3–4.5 (1H, m).

EXAMPLE 5

Preparation of N-[(R)-1-ethoxycarbonyl-2-(1-adamantylthio)ethyl]-alanyl-(S)-proline (β-isomer) and L-arginine salt thereof.

Following the general procedure of Reference Example 8, the title compound was prepared as colorless amorphous solids from 632 mg of β-isomer of N-[(R)-1-ethoxycarbonyl-2-(1-adamantylthio)ethyl]-alanyl-(S)-proline t-butyl ester obtained in Example 1. Yield 470 mg.

The compound (470 mg) obtained in the foregoing reaction was dissolved in 5 ml of ethanol. To the solution was added a solution of 181 mg of L-arginine in 2 ml of water with stirring. The water and ethanol were distilled off and the residue was dried under reduced pressure, giving the L-arginine salt of the title compound as colorless powder. Yield 309 mg. M.p 115°–120° C.

$[\alpha]_D^{26} = -32.5°$ (c=0.5, ethanol).

EXAMPLES 6 TO 8

The compounds as listed below in Table 3 were obtained by following the general procedure of Example 5.

Of the two isomers produced as the reaction products of S-(N-substituted carbamoylmethyl)-L-cysteine ethyl ester and 2-bromopropionic acid t-butyl ester, a first eluate obtained in silica gel column chromatography (using ether/n-hexane) is hereinafter referred to as "α-isomer", and a second eluate therefrom as "β-isomer". Also hereinafter the compounds derived from the α-isomer are called "α-isomers" and those from the β-isomer are called "β-isomers".

REFERENCE EXAMPLE 13

Preparation of N-[(R)-1-ethoxycarbonyl-2-cyclopentylcarbamoylmethylthioethyl]-alanine t-butyl ester (α- and β-isomers)

A 2.8 ml of triethylamine was added to a solution of 5.5 g of S-cyclopentylcarbamoylmethyl-L-cysteine ethyl ester and 4.2 g of 2-bromopropionic acid t-butyl ester in 10 ml of HMPA. The mixture was stirred at room temperature for 30 hours. The reaction mixture was poured into ice water and the mixture was extracted with ethyl acetate. The extract was sufficiently washed with water and dried over anhydrous sodium sulfate. The solvent was distilled off under reduced pressure. The residue was purified by silica gel column chromatography (a 10:1 mixture of ether and n-hexane as an eluent), producing the α-isomer of the title compound from the first eluate as a colorless oil. Yield 1.36 g.

$[\alpha]_D^{26} = +28.6°$ (c=0.9, ethanol)

NMR (CDCl$_3$): δ1.27 (3H, d, J=7 Hz), 1.29 (3H, t, J=7 Hz), 1.45 (9H, s), 1.5–2.1 (8H, m), 2.83 (2H, d, J=6 Hz), 3.26 (2H, s), 4.21 (2H, q, J=7 Hz)

The β-isomer of the title compound was obtained from the second eluate as a colorless oil. Yield 1.94 g.

TABLE 3

$$R_1-S-CH_2\overset{(R)}{\underset{COOC_2H_5}{CH}}-NH-\overset{CH_3}{\underset{*}{CH}}-CO-N\underset{(S)}{\diagdown}\text{COOH},\beta\text{-isomer}$$

| Example No. | R$_1$ | Optical Rotation | NMR(CDCl$_3$): δ or melting point |
|---|---|---|---|
| 6 | (indanyl) (Maleate) | $[\alpha]_D^{25} = -45.1°$ (c = 0.8, ethanol) | 47–55° C. |
| 7 | (cyclopentyl) (Maleate) | $[\alpha]_D^{24} = -58.5°$ (c = 0.6, ethanol) | 81–83° C. |
| 8 | (1-methylcyclohexyl) CH$_3$ (Maleate) | $[\alpha]_D^{23} = -43.6°$ (c = 0.6, ethanol) | 1.31 (3H, t, J=8Hz), 1.34 (3H, s), 1.3–2.5 (17H, m) 3.0–3.9 (6H, m), 4.22 (2H, q, J=8Hz), 4.5–4.8 (1H, m), 6.28 (2H, s) |

In Reference Examples 13 to 26 and Examples 9 to 26, the terms "α-isomer" and "β-isomer" are used to mean the following.

$[\alpha]_D^{26} = -33.4°$ (c=0.6, ethanol)

NMR (CDCl$_3$): δ1.29 (3H, d, J=7 Hz), 1.29 (3H, t, J=7 Hz), 1.47 (9H, s), 1.5–2.2 (8H, m), 3.26 (2H, s), 4.21 (2H, q, J=7 Hz)

REFERENCE EXAMPLE 14

Preparation of N-[(R)-1-ethoxycarbonyl-2benzylcarbamoylmethylthioethyl]-(R,S)-alanine t-butyl ester In 5 ml of HMPA were dissolved 2.2 g of S-benzylcarbamoylmethyl-L-cysteine ethyl ester and 1.6 g of 2-bromopropionic acid t-butyl ester. A 1.0 ml quantity of triethylamine was added to the solution and the mixture was stirred at room temperature for 34 hours. The reaction mixture was poured into ice water and the mixture was extracted with ethyl acetate. The extract was sufficiently washed with water and dried over anhydrous sodium sulfate. The solvent was distilled off under reduced pressure and the residue was purified by silica gel column chromatography (a 40:1 mixture of chloroform and methanol as an eluent), giving the title compound as a colorless oil. Yield 2.3 g.

$[\alpha]_D^{23} = -9.6°$ (c=0.9, ethanol)

NMR (CDCl$_3$): δ1.19 (3H, d, J=7 Hz), 1.27 (3H, t, J=7 Hz), 1.43 (9H, s), 3.34 (2H, s), 4.18 (2H, q, J=7 Hz), 4.44, 4.45 (total 2H, each s), 7.30 (5H, s)

REFERENCE EXAMPLES 15 TO 17

The compounds as listed below in Table 4 were obtained by following the general procedure of Reference Example 14.

REFERENCE EXAMPLE 18

Preparation of N-[(R)-1-ethoxycarbonyl-2-cyclopentylcarbamoylmethylthioethyl]-alanine (β-isomer)

In 5 ml of 25% HBr-acetic acid was dissolved 1.84 g of the β-isomer of N-[(R)-1-ethoxycarbonyl-2-cyclopentylcarbamoylmethylthioethyl]-alanine t-butyl ester prepared in Reference Example 13. The solution was stirred at room temperature for 1 hour. The HBr-acetic acid was evaporated off under reduced pressure. The residue was poured into ice water and the mixture was adjusted to a pH of 4 with a saturated aqueous solution of sodium hydrogencarbonate. Then the mixture was extracted with chloroform. The extract was washed with water and dried over anhydrous sodium sulfate. The solvent was distilled off under reduced pressure. To the residue was added ether to precipitate crystals which were collected by filtration as the title compound. Yield 670 mg. M.p. 119°–121° C.

$[\alpha]_D^{23} = -31.9°$ (c=0.5, ethanol)

REFERENCE EXAMPLES 19 TO 22

The compounds as listed below in Table 5 were obtained by following the general procedure of Reference Example 8.

TABLE 4

$$\begin{array}{c} R_5 \\ \phantom{R_5}\diagdown \\ \phantom{R_5}\phantom{\diagdown}N-\underset{\underset{O}{\|}}{C}-CH_2-S-CH_2\underset{(R)}{CH}-NH-\underset{\underset{CO_2C_2H_5}{|}}{\overset{\overset{CH_3}{|}}{CH}}-CO_2-C(CH_3)_3 \\ \phantom{R_5}\diagup \\ R_6 \end{array}$$
(R,S)

| Ref. Ex. No. | R$_5$ | R$_6$ | Optical Rotation (Solvent: ethanol) | NMR(CDCl$_3$):δ |
|---|---|---|---|---|
| 15 | Ph— | H | $[\alpha]_D^{23} = -1.2°$ (c = 2) | 1.1–1.4 (6H, m), 1.44 (9H, s), 3.46 (2H, s), 3.1–3.7 (2H, m), 4.21 (2H, q, J=7Hz), 7.1–7.7 (5H, m) |
| 16 | Ph— | CH$_3$ | $[\alpha]_D^{23} = -11.4°$ (c = 1.6) | 1.26 (3H, d, J=7Hz), 1.26 (3H, t, J=Hz), 1.44 (9H, s), 2.7–3.7 (7H, m), 3.28 (2H, s), 4.17 (2H, q, J=7Hz), 7.1–7.5 (5H, m) |
| 17 | —(CH$_2$)$_5$— | | $[\alpha]_D^{19} = -8.7°$ (c = 1.1) | 1.29 (3H, t, J=7Hz), 1.2–1.4 (3H, m), 1.44, 1.46 (total 9H, each s), 1.5–1.7 (6H, m), 2.8–3.7 (8H, m), 3.40 (2H, s), 4.20 (2H, q, J=7Hz) |

TABLE 5

$$\begin{array}{c} R_5 \\ \phantom{R_5}\diagdown \\ \phantom{R_5}\phantom{\diagdown}N-\underset{\underset{O}{\|}}{C}-CH_2-S-CH_2\underset{(R)}{CH}-NH-\underset{\underset{CO_2C_2H_5}{|}}{\overset{\overset{CH_3}{|}}{CH}}-CO_2H \\ \phantom{R_5}\diagup \\ R_6 \end{array}$$
(R,S)

| Ref. Ex. No. | R$_5$ | R$_6$ | Optical Rotation or Melting Point | NMR:δ |
|---|---|---|---|---|
| 19 | PhCH$_2$— | H | $[\alpha]_D^{23} = -11.2°$ (c = 0.6, ethanol) | Solvent: CDCl$_3$ + CD$_3$OD 1.29 (3H, t, J=7Hz), 1.33 (3H, d, J=7Hz), 2.8–3.8 (4H, m), 3.34 (2H, s), 4.20, 4.22 (total 2H, each q, J=7Hz), 4.43 (2H, s), 7.42 (5H, s) |
| 20 | Ph— | H | $[\alpha]_D^{23} = -1.2°$ (c = 2, ethanol) 156–159° C. (decomposition) | Solvent: DMSO-d$_6$ 1.15 (3H, d, J=7Hz), 1.17 (3H, t, J=7Hz), 2.90 (2H, d, J=6Hz), 3.29 (1H, q, J=7Hz), 3.34 (2H, s), |

TABLE 5-continued $$\begin{array}{c} R_5 \\ \diagdown \\ R_6 \end{array} N-\overset{O}{\underset{\|}{C}}-CH_2-S-\overset{(R)}{CH_2CH}-NH-\overset{CH_3}{\underset{|}{CH}}-CO_2H \\ \phantom{xxxxxxxxxxxxxxxx} | \phantom{xxxxxxx} (R,S) \\ \phantom{xxxxxxxxxxxxxxxx} CO_2C_2H_5$$

| Ref. Ex. No. | $R_5$ | $R_6$ | Optical Rotation or Melting Point | NMR: δ |
|---|---|---|---|---|
| 21 | Ph— | CH$_3$ | $[\alpha]_D^{23}=-9.5°$ (c = 0.7, DMF) | 3.53 (1H, t, J=6Hz), 4.16 (2H, q, J=7Hz), 6.9–7.6 (5H, m) Solvent: CDCl$_3$ 1.27, 1.29 (total 3H, each t, J=7Hz), 1.49 (3H, d, J=7Hz), 2.8–3.9 (7H, m), 3.29 (2H, s), 4.19, 4.22 (total 2H, each q, J=7Hz), 6.61 (1H, brs), 7.2–7.5 (5H, m) |
| 22 | —(CH$_2$)$_5$— | | $[\alpha]_D^{23}=-17.3°$ (c = 1.2, ethanol) 59–61° C. | Solvent: CD$_3$OD 1.31 (3H, t, J=7Hz), 1.45, 1.48 (total 3H, each d, J=7Hz), 1.5–1.8 (6H, m), 2.9–4.1 (8H, m), 3.56 (2H, s), 4.27 (2H, q, J=7Hz) |

REFERENCE EXAMPLE 23

Preparation of N-[(R)-1-ethoxycarbonyl-2-(N-benzyl-N-isopropylcarbamoylmethylthio)ethyl]-(R,S)-alanine A 13 g quantity of pyruvic acid was added to a solution of 10 g of S-(N-benzyl-N-isopropylcarbamoylmethyl)-L-cysteine ethyl ester in 30 ml of ethanol and 10 ml of water with ice cooling. The mixture was adjusted to a pH of 7 with a 4N aqueous solution of sodium hydroxide. A 3.7 g quantity of sodium cyanoborohydride was gradually added thereto and the mixture was stirred at room temperature overnight. The solvent was evaporated off under reduced pressure. The residue was poured into ice water and the pH was adjusted to 8 with a saturated aqueous solution of sodium hydrogencarbonate. The solution was washed with ether and the aqueous layer was adjusted to pH 4 with 10% hydrochloric acid and extracted with ethyl acetate. The extract was washed with water and dried over anhydrous sodium sulfate. The solvent was distilled off under reduced pressure and the residue was purified by silica gel column chromatography (a 15:1 mixture of chloroform and methanol as an eluent), giving the title compound. Yield 2.8 g.

$[\alpha]_D^{20}=+3.2°$ (c=1.0, ethanol)

NMR (CDCl$_3$): δ1.12 (3H, d, J=7 Hz), 1.18 (3H, d, J=7 Hz), 1.31 (3H, d, J=7 Hz), 1.34 (3H, t, J=7 Hz), 2.9–3.8 (7H, m), 4.18, 4.21 (total 2H, each q, J=7 Hz), 4.53 (2H, s), 6.74 (1H, brs), 7.23 (5H, s)

REFERENCE EXAMPLES 24 TO 26

The compounds as listed below in Table 6 were obtained by following the general procedure of Reference Examples 23.

TABLE 6

$$\begin{array}{c} R_5 \\ \diagdown \\ R_6 \end{array} N-\overset{O}{\underset{\|}{C}}-CH_2-S-\overset{(R)}{CH_2CH}-NH-\overset{CH_3}{\underset{|}{CH}}-CO_2H \\ \phantom{xxxxxxxxxxxxxxxx} | \phantom{xxxxxxx} (R,S) \\ \phantom{xxxxxxxxxxxxxxxx} CO_2C_2H_5$$

| Ref. Ex. No. | $R_5$ | $R_6$ | Optical Rotation | NMR: δ |
|---|---|---|---|---|
| 24 | Ph— | PhCH$_2$— | $[\alpha]_D^{19}=+6.7°$ (c = 0.9, ethanol) | Solvent: CDCl$_3$ 1.25 (3H, t, J=7Hz), 1.37 (3H, d, J=7Hz), 2.9–3.8 (6H, m), 4.17 (2H, q, J=7Hz), 4.87 (2H, s), 6.50 (1H, brs), 7.0–7.4 (10H, m) |
| 25 | n-propyl | n-propyl | $[\alpha]_D^{17}=-1.1°$ (c = 0.7, ethanol) | Solvent: CDCl$_3$ 0.89 (3H, t, J=7Hz), 0.92 (3H, t, J=7Hz), 1.29 (3H, t, J=7Hz), 1.42 (3H, d, J=7Hz), 1.2–1.8 (4H, m), 3.0–3.8 (10H, m), 4.21 (2H, q, J=7Hz), 6.85 (1H, brs) |
| 26 | α-naphthyl | H | $[\alpha]_D^{22}=+5.0°$ (c = 1.3, DMF) | Solvent: CD$_3$OD 1.1–1.5 (6H,m), 3.20 (2H, d, J=6Hz), 3.59 (2H, s), 3.4–4.1 (2H, m), 4.20, 4.22 (total 2H, each q, J=7Hz), 7.4–8.1 (7H, m) |

EXAMPLE 9

Preparation of N-[(R)-1-ethoxycarbonyl-2-cyclopentylcarbamoylmethylthioethyl]-alanyl-(S)-proline t-butyl ester (β-isomer)

In 5 ml of DMF were dissolved 600 mg of the β-isomer of N-[(R)-1-ethoxycarbonyl-2-cyclopentylcarbamoylmethylthioethyl]-alanine obtained in Reference Example 18 and 330 mg of (S)-proline t-butyl ester. To the stirred solution was added with ice cooling a solution of 314 mg of DEPC (conc. 90%) in 2 ml of DMF. A solution of 0.3 ml of triethylamine in 1 ml of DMF was added dropwise thereto. The mixture was stirred with ice cooling for 2 hours and then further stirred at room temperature for 10 hours. The reaction mixture was poured into ice water and extracted with ethyl acetate. The extract was washed with water and dried over anhydrous sodium sulfate. The solvent was distilled off under reduced pressure and the residue was purified by silica gel column chromatography (a 35:1 mixture of chloroform and methanol as an eluent), giving the title compound as a colorless oil.

Yield 740 mg.

$[\alpha]_D^{26} = -87.9°$ (c=0.4, ethanol)

NMR (CDCl$_3$): δ1.29 (3H, d, J=7 Hz) 1.29 (3H, t, J=7 Hz) 1.44, 1.46 (total 9H, each s), 1.5–2.2 (12H, m), 3.26 (2H, s), 4.22 (2H, q, J=7 Hz), 4.3–4.5 (1H, m)

EXAMPLES 10 TO 17

The compounds as listed below in Table 7 were obtained by following the general procedure of Example 9.

TABLE 7

$$R_5\text{\textbackslash}N\text{-}\underset{R_6}{\overset{O}{\overset{\|}{C}}}\text{-}CH_2\text{-}S\text{-}\underset{CO_2C_2H_5}{\overset{(R)}{CH_2CH}}\text{-}NH\text{-}\underset{(R,S)}{\overset{CH_3}{\overset{|}{CH}}}\text{-}CO\text{-}N\underset{(S)}{\diagdown}$$
with $CO_2-C(CH_3)_3$

| Example No. | R$_5$ | R$_6$ | Optical Rotation (Solvent: ethanol) | NMR(CDCl$_3$):δ |
|---|---|---|---|---|
| 10 | PhCH$_2$— | H | $[\alpha]_D^{24} = -50.9°$ (c = 0.6) | 1.1–1.3 (6H, m), 1.41, 1.42 (total 9H, each s), 4.16, 4.18 (total 2H, each q, J=7Hz), 4.3–4.4 (1H, m), 4.44, 4.51 (total 2H, each s), 7.30 (5H, s) |
| 11 | Ph— | H | $[\alpha]_D^{23} = -21.3°$ (c = 0.7) | 1.23 (3H, t, J=7Hz), 1.23 (3H, d, J=7Hz), 1.43, 1.46 (total 9H, each s), 4.18 (2H, q, J=7Hz), 4.4–4.5 (1H, m), 7.0–7.7 (5H, m) |
| 12 | Ph— | CH$_3$— | $[\alpha]_D^{24} = -63.5°$ (c = 0.7) | 1.26 (3H, t, J=7Hz), 1.27 (3H, d, J=7Hz), 1.43, 1.45 (total 9H, each s), 3.27 (2H, s), 4.16, 4.17 (total 2H, each q, J=7Hz), 4.4–4.5 (1H, m), 7.2–7.5 (5H, m) |
| 13 | PhCH$_2$— | isopropyl | $[\alpha]_D^{20} = -30.1°$ (c = 1.0) | 1.0–1.4 (12H, m), 1.43 (9H, s), 1.6–4.0 (13H, m), 4.16 (2H, q, J=7Hz), 4.53 (2H, s), 4.6–4.9 (1H, m), 7.23 (5H,s) |
| 14 | Ph— | PhCH$_2$— | $[\alpha]_D^{19} = -25.2°$ (c = 0.8) | 1.1–1.3 (6H, m), 1.43, 1.46 (total 9H, each s), 1.6–4.0 (12H, m), 4.15 (2H, q, J=7Hz), 4.4–4.5 (1H, m), 4.88 (2H, s), 7.0–7.4 (10H, m) |
| 15 | n-propyl | n-propyl | $[\alpha]_D^{19} = -44.5°$ (c = 1.0) | 0.91 (6H, t, J=7Hz), 1.28 (3H, t, J=7Hz), 1.44, 1.46 (total 9H, each s), 1.2–1.8 (7H, m), 1.9–4.0 (16H, m), 4.16, 4.19 (total 2H, each q, J=7Hz), 4.4–4.5 (1H, m) |
| 16 | α-naphthyl | H | $[\alpha]_D^{20} = -27.0°$ (c = 0.5) | 1.1–1.4 (6H, m), 1.40, 1.43 (total 9H, each s), 1.6–2.2 (4H, m), 4.16, 4.18 (total 2H, each q, J=7Hz), 4.3–4.5 (1H, m), 7.3–8.1(7H, m) |
| 17 | —(CH$_2$)$_5$— | | $[\alpha]_D^{20} = -62.1°$ (c = 0.6) | 1.24 (3H, d, J=7Hz), 1.26 (3H, t, J=7Hz), 1.44, 1.46 (total 9H, each s), 1.5–2.3 (10H, m), 4.19 (2H, q, J=7Hz), 4.4–4.5 (1H, m) |

EXAMPLE 18

Preparation of N-[(R)-1-ethoxycarbonyl-2-cyclopentylcarbamoylmethylthioethyl]-alanyl-(S)-proline (β-isomer) and maleate thereof In 1.5 ml of 25% HBr-acetic acid was dissolved 580 mg of the β-isomer of N-[(R)-1-ethoxycarbonyl-2-cyclopentylcarbamoylmethylthioethyl]-alanyl-(S)-proline t-butyl ester prepared in Example 9. The solution was stirred at room temperature for 1 hour. The HBr-acetic acid was distilled off under reduced pressure and the residue was poured into ice water and adjusted to a pH of 4 with a saturated aqueous solution of sodium hydrogencarbonate. The mixture was extracted with methylene chloride. The extract was washed with water and dried over anhydrous sodium sulfate. The solvent was distilled off under reduced pressure, giving the title compound as a colorless oil. Yield 546 mg.

The compound obtained above (540 mg) was dissolved in 5 ml of THF. To the solution was added a solution of 140 mg of maleic acid in 10 ml of THF. The solvent was distilled off under reduced pressure and ether was added to the residue. The crystals thus precipitated were collected by filtration and recrystallized from THF-ether, producing the maleate of the title compound. Yield 215 mg.

$[\alpha]_D^{22} = -48.0°$ (c=1.4, ethanol)

NMR (CD$_3$OD): δ1.29 (3H, d, J=7 Hz), 1.29 (3H, t, J=7 Hz), 1.4–2.2 (12H, m), 3.26 (2H, s), 4.20 (2H, q, J=7 Hz), 4.3–4.5 (1H, m), 6.26 (2H, s)

EXAMPLES 19 TO 26

The compounds as listed below in Table 8 were obtained by following the general procedure of Example 18.

REFERENCE EXAMPLES 27

Preparation of N-benzyloxycarbonyl-(S)-prolyl-(S)-proline t-butyl ester

In 15 ml of DMF were dissolved 5.0 g of N-benzyloxycarbonyl-(S)-proline, 3.4 g of (S)-proline t-butyl ester, 4.0 g of WSCD.HCl and 2.7 g of HOBt. To the solution was added 2.8 ml of triethylamine with ice cooling. The mixture was stirred overnight and the reaction mixture was poured into ice water, followed by extraction with ethyl acetate. The extract was washed successively with 10% hydrochloric acid, water, a saturated aqueous solution of sodium hydrogencarbonate and water in this sequence. The mixture was dried over anhydrous sodium sulfate. The solvent was distilled off under reduced pressure and the residue was crystallized from n-hexane. Yield 6.9 g. M.p. 89° to 90.5° C.

$[\alpha]_D^{18} = -107.1°$ (c=0.9, ethanol)

REFERENCE EXAMPLE 28

Preparation of (S)-prolyl-(S)-proline t-butyl ester hydrochloride

A 6.5 g quantity of N-benzyloxycarbonyl-(S)-prolyl-(S)-proline t-butyl ester prepared in Reference Example 27 was dissolved in 30 ml of isopropyl alcohol. The solution was subjected to catalytic reduction using about 2 g of 10% palladium-carbon as a catalyst. After completion of the reaction, the catalyst was removed by filtration and the solvent was distilled off under reduced pressure. The residue was dissolved in 15 ml of ether and 4.5 ml of 4N-HCl-ethyl acetate was added to the solution with ice cooling. The precipitated crystals were collected by filtration and dried under reduced pressure.

Yield 4.1 g.

TABLE 8

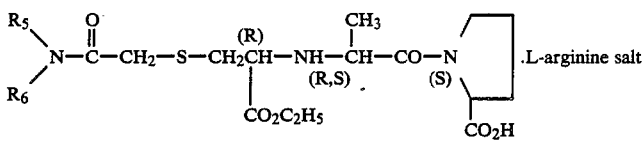
.L-arginine salt

| Example No. | R$_5$ | R$_6$ | Optical Rotation | NMR (CD$_3$OD): δ or Melting point (Recrystallization solvent) |
|---|---|---|---|---|
| 19 | Ph— | H | $[\alpha]_D^{23} = -7.5°$ (c = 0.9, ethanol) | 67–80° C. (ethanol-ether) |
| 20 | PhCH$_2$— | isopropyl | $[\alpha]_D^{23} = -27.1°$ (c = 1.0, ethanol) | 76–92° C. (ethyl acetate-ether) |
| 21 | Ph— | PhCH$_2$— | $[\alpha]_D^{17} = -20.7°$ (c = 1.0, ethanol) | 60–73° C. (ethyl acetate-ether) |
| 22 | n-propyl | n-propyl | $[\alpha]_D^{15} = -28.0°$ (c = 0.9, ethanol) | 58–71° C. (ethyl acetate-ether) |
| 23 | Ph— | CH$_3$— | $[\alpha]_D^{23} = -41.9°$ (c = 1.2, ethanol) | 1.1–1.4 (6H, m), 1.5–2.3 (8H, m), 2.36 (2H, s), 4.14, 4.16 (total 2H, each q, J=7Hz), 4.2–4.4 (1H, m), 7.2–7.7 (5H, m) |
| 24 | PhCH$_2$— | H | $[\alpha]_D^{23} = -41.7°$ (c = 1.1, water) | 1.1–1.4 (6H, m, 1.5–2.4 (8H, m), 4.16, 4.18 (total 2H, each q, J=7Hz), 4.3–4.5 (1H, m), 4.39 (2H, s), 7.29 (5H, s) |
| 25 | α-naphthyl | H | $[\alpha]_D^{23} = -6.3°$ (c = 1.4, 90% ethanol) | 1.1–1.4 (6H, m), 1.5–2.3 (8H, m), 4.16, 4.18 (total 2H, each q, J=7Hz), 4.3–4.5 (1H, m), 7.4–8.2 (7H, m) |
| 26 | —(CH$_2$)$_5$— | | $[\alpha]_D^{23} = -42.7°$ (c = 0.5, ethanol) | 1.21, 1.28 (total 3H, each d, J=7Hz), 1.28 (3H, t, J=7Hz), 1.4–2.4 (14H, m), 4.17, 4.19 (total 2H, each q, J=7Hz), 4.3–4.5 (1H, m) |

In Reference Examples 27 to 50, and Examples 27 to 61, the terms "α-isomer" and "β-isomer" are used to mean the following.

Of the two isomers produced as the reaction products of S-alkyl-L-cysteine ethyl ester and 2-bromopropionic acid t-butyl ester, as first eluate obtained in silica gel column chromatography (using ether/n-hexane) is hereinafter referred to as "α-isomer", and a second eluate therefrom as "β-isomer". Also hereinafter the compounds derived from the α-isomer are called "α-isomers" and those from the β-isomer are called "β-isomers".

$[\alpha]_D^{18} = -140.1°$ (c=0.5, ethanol)

REFERENCE EXAMPLE 29

(a) Preparation of
N-[(R)-1-ethoxycarbonyl-2-heptylthioethyl]-alanine
t-butyl ester (α- and β-isomers)

In 20 ml of HMPA were dissolved 5.9 g of S-heptyl-L-cysteine ethyl ester and 5.5 g of 2-bromopropionic acid t-butyl ester. A 3.4 ml quantity of triethylamine was added to the solution. The mixture was stirred at room temperature for 24 hours. The reaction mixture was poured into ice water, followed by extraction with ethyl acetate. The extract was sufficiently washed with water and dried over anhydrous sodium sulfate. The solvent was distilled off under reduced pressure and the residue was separated and purified by silica gel column chromatography (a 1:3 mixture of ether and n-hexane as an eluent), producing the α-isomer of the title compound as a colorless oil from the first eluate. Yield 2.8 g.

$[\alpha]_D^{20} = +26.9°$ (c=0.9, ethanol)

NMR (CDCl$_3$): δ0.88 (3H, t, J=5 Hz), 1.27 (3H, d, J=7 Hz), 1.29 (3H, t, J=7 Hz), 1.4–1.8 (10H, m), 1.45 (9H, s), 2.55 (2H, t, J=7 Hz), 2.80 (2H, d, J=6 Hz), 3.32 (1H, q, J=7 Hz), 3.46 (1H, t, J=7 Hz), 4.20 (2H, q, J=7 Hz)

The β-isomer of the title compound was obtained from the second eluate as a colorless oil. Yield 2.6 g.

$[\alpha]_D^{20} = -38.6°$ (c=1.3, ethanol)

NMR (CDCl$_3$): δ0.88 (3H, t, J=7 Hz), 1.29 (3H, t, J=7 Hz), 1.30 (3H, d, J=7 Hz), 1.4–1.8 (10H, m), 1.47 (9H, s), 2.54 (2H, t, J=7 Hz), 2.70 (1H, d—d, J=13 Hz, 7.5 Hz), 2.92 (1H, d—d, J=13 Hz, 5 Hz), 3.29 (1H, q, J=7 Hz), 3.47 (1H, d—d, J=5 Hz, 7.5 Hz), 4.21 (2H, q, J=7 Hz)

(b) Preparation of
N-[(R)-1-ethoxycarbonyl-2-heptylthioethyl]-alanine
(β-isomer)

The β-isomer of N-[(R)-1-ethoxycarbonyl-2-heptylthioethyl]-alanine t-butyl ester (2.4 g) prepared above was dissolved in 10 ml of TFA and the solution was stirred at room temperature for 3 hours. The TFA was evaporated off under reduced pressure. The residue was poured into ice water and adjusted to a pH of 4 with a saturated aqueous solution of sodium hydrogencarbonate, followed by extraction with methylene chloride. The extract was washed with water and dried over anhydrous sodium sulfate. The solvent was distilled off under reduced pressure and the residue was recrystallized from methylene chloride-ether, giving the β-isomer of the title compound. Yield 1.8 g. M.p. 124° to 126° C.

$[\alpha]_D^{23} = -25.1°$ (c=0.7, DMF)

EXAMPLE 27

Preparation of
N-[(R)-1-ethoxycarbonyl-2-heptylthioethyl]-alanyl-(S)-prolyl-(S)-proline t-butyl ester (β-isomer)

In 25 ml of DMF were dissolved 2.6 g of the β-isomer of N-[(R)-1-ethoxycarbonyl-2-heptylthioethyl]-alanine prepared in Reference Example 29, 2.5 g of (S)-prolyl-(S)-proline t-butyl ester prepared in Reference Example 28, 1.7 g of WSCD.HCl and 1.1 g of HOBt. To the solution was added 3.6 ml of triethylamine while being stirred with ice cooling. The solution was stirred overnight. The reaction mixture was poured into ice water, followed by extraction with ethyl acetate. The extract was washed with a saturated aqueous solution of sodium hydrogencarbonate and then with a saturated aqueous solution of sodium chloride and dried over anhydrous sodium sulfate. The solvent was distilled off under reduced pressure and the residue was purified by silica gel column chromatography (a 30:1 mixture of chloroform and methanol as an eluent), giving the title compound as a colorless oil. Yield 3.5 g.

$[\alpha]_D^{20} = -121.5°$ (c=1.0, ethanol)

NMR (CDCl$_3$): δ0.87 (3H, t, J=5.5 Hz), 1.1–1.4 (16H, m), 1.43 (9H, s), 1.7–2.2 (8H, m), 2.52 (2H, t, J=7 Hz), 3.3–3.9 (6H, m), 4.20 (2H, q, J=7 Hz), 4.4–4.6 (1H, m), 4.6–4.8 (1H, m)

EXAMPLES 28 TO 31

The compounds as listed below in Table 9 were obtained by following the general procedure of Example 27.

TABLE 9

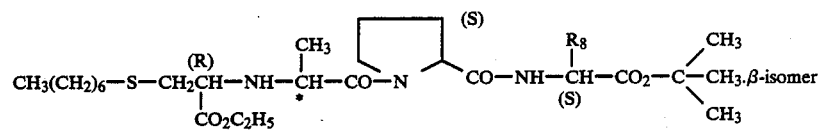

| Example No. | R$_8$ | Optical Rotation (Solvent: ethanol) | NMR(CDCl$_3$):δ |
|---|---|---|---|
| 28 | H | $[\alpha]_D^{20} = -77.0°$ (c = 0.5) | 0.88 (3H, t, J=5.5Hz), 1.2–1.4 (16H, m), 1.44 (9H, s), 1.7–2.2 (4H, m), 3.3–3.8 (4H, m), 4.19 (2H, q, J=7Hz), 4.2–4.4 (1H, m), 4.5–4.7 (1H, m) |
| 29 | CH$_3$ | $[\alpha]_D^{20} = -98.8°$ (c = 0.9) | 0.88 (3H, t, J=5.5Hz), 1.2–1.5 (19H, m), 1.45 (9H, m), 1.8–2.2 (4H, m), 3.3–3.8 (4H, m), 4.19 (2H, q, J=7Hz), 4.2–4.4 (1H, m), 4.5–4.7 (1H, m), |

TABLE 9-continued $$CH_3(CH_2)_6-S-\overset{(R)}{\underset{CO_2C_2H_5}{CH_2CH}}-NH-\overset{CH_3}{\underset{*}{CH}}-CO-N\underset{(S)}{\overset{\text{(S)}}{\bigcirc}}CO-NH-\overset{R_8}{\underset{(S)}{CH}}-CO_2-C\underset{CH_3}{\overset{CH_3}{\diagup}}CH_3\cdot\beta\text{-isomer}$$

| Example No. | $R_8$ | Optical Rotation (Solvent: ethanol) | NMR(CDCl$_3$):δ |
|---|---|---|---|
| 30 | CH$_3$\\CH/CH$_3$ | $[\alpha]_D^{20} = -89.6°$ (c = 0.7) | 0.86 (6H, d, J=7Hz), 1.1–1.4 (16H, m), 1.46 (9H, s), 1.8–2.2 (4H, m), 2.53 (2H, t, J=7Hz), 3.3–3.8 (4H, m), 4.19 (2H, q, J=7Hz), 4.2–4.4 (1H, m), 4.5–4.7 (1H, m) |
| 31 | PhCH$_2$ | — | 0.87 (3H, t, J=5.5Hz), 1.2–1.4 (16H, m), 1.45 (9H, s), 1.8–2.3 (4H, m), 2.52 (2H, t, J=7Hz), 3.1–3.7 (6H, m), 4.20 (2H, q, J=7Hz), 4.2–4.4 (1H, m), 4.5–4.7 (1H, m), 7.19 (5H, s) |

REFERENCE EXAMPLE 30

(a) Preparation of N-[(R)-1-ethoxycarbonyl-2-pentylthioethyl]-alanine t-butyl ester (α- and β-isomers)

In 20 ml of HMPA were dissolved 8.6 g of S-pentyl-L-cysteine ethyl ester and 8.2 g of 2-bromopropionic acid t-butyl ester. To the solution was added 5.5 ml of triethylamine. The solution was stirred at room temperature for 24 hours. The reaction mixture was poured into ice water, followed by extraction with ethyl acetate. The extract was sufficiently washed with water and dried over anhydrous sodium sulfate. The solvent was distilled off under reduced pressure and the residue was purified by silica gel column chromatography (a 1:2 mixture of ether and n-hexane as an eluent), producing the α-isomer of the title compound as a colorless oil from the first eluate. Yield 3.9 g.

$[\alpha]_D^{25} = +28.6°$ (c=1.0, ethanol)

NMR (CDCl$_3$): δ0.90 (3H, t, J=5.5 Hz), 1.28 (3H, d, J=7 Hz), 1.29 (3H, t, J=7 Hz), 1.45 (9H, s), 1.3–1.8 (6H, m), 2.56 (2H, t, J=7 Hz), 2.81 (2H, d, J=6 Hz), 3.32 (1H, q, J=7 Hz), 3.46 (1H, t, J=6 Hz), 4.20 (2H, q, J=7 Hz)

Product from the second eluate (β-isomer)
Yield 3.6 g.

$[\alpha]_D^{25} = -42.2°$ (c=1.0, ethanol)

NMR (CDCl$_3$): δ0.90 (3H, t, J=5.5 Hz), 1.30 (3H, d, J=7 Hz), 1.30 (3H, t, J=7 Hz), 1.47 (9H, s), 1.3–1.8 (6H, m), 2.23 (1H, brs), 2.54 (2H, t, J=7 Hz), 2.70 (1H, d—d, J=13 Hz, 8 Hz), 2.92 (1H, d—d, J=13 Hz, 5.5 Hz), 3.29 (1H, q, J=7 Hz), 3.45 (1H, d—d, J=8 Hz, 5.5 Hz), 4.21 (2H, q, J=7 Hz)

(b) Preparation of N-[(R)-1ethoxycarbonyl-2-pentylthioethyl]-alanine (β-isomer)

The β-isomer of N-[(R)-1-ethoxycarbonyl-2-pentylthioethyl]-alanine t-butyl ester (800 mg) obtained above was dissolved in 5 ml of TFA and the solution was stirred at room temperature for 3 hours. The TFA was evaporated off under reduced pressure. The residue was poured into ice water and adjusted to a pH of 4 with a saturated aqueous solution of sodium hydrogencarbonate, followed by extraction with methylene chloride. The extract was washed with water and dried over anhydrous sodium sulfate. The solvent was distilled off under reduced pressure and the residue was recrystallized from methylene chloride, giving the β-isomer of the title compound. Yield 580 mg. M.p. 124° to 125° C.

$[\alpha]_D^{21} = -28.1°$ (c=0.9, DMF)

EXAMPLE 32

Preparation of N-[(R)-1-ethoxycarbonyl-2pentylthioethyl]-alanyl-(S)-prolyl-(S)-proline t-butyl ester (β-isomer)

Following the general procedure of Example 27, the title compound was prepared as a colorless oil from 700 mg of the β-isomer of N-[(R)-1-ethoxycarbonyl-2-pentylthioethyl]-alanine prepared in Reference Example 30 and 730 mg of the hydrochloride of (S)-prolyl-(S)-proline t-butyl ester prepared in Reference Example 28. Yield 930 mg.

$[\alpha]_D^{20} = -144.4°$ (c=0.4, ethanol)

NMR (CDCl$_3$): δ0.89 (3H, t, J=5.5 Hz), 1.1–1.4 (12H, m), 1.43 (9H, s), 1.8–2.3 (8H, m), 2.52 (2H, t, J=7 Hz), 3.3–3.9 (6H, m), 4.20 (2H, q, J=7 Hz), 4.3–4.5 (1H, m), 4.5–4.8 (1H, m)

EXAMPLE 33

Preparation of N-[(R)-1-ethoxycarbonyl-2hepthylthioethyl]-alanyl-(S)-prolyl-(S)-proline (β-isomer) and L-arginine salt thereof In 10 ml of 25% HBr-acetic acid was dissolved 3.1 g of the β-isomer of N-[(R)-1-ethoxycarbonyl-2-heptyl-thioethyl]-alanyl-(S)-prolyl-(S)-proline t-butyl ester obtained in Example 27. The solution was stirred at room temperature for 2 hours. The solvent was distilled off under reduced pressure and the residue was made weakly alkaline with a saturated aqueous solution of sodium hydrogencarbonate. The solution was washed with ether, and the aqueous layer was adjusted to a pH of 4 with 10% hydrochloric acid, and extracted with methylene chloride. The extract was washed several times with water and dried over anhydrous sodium sulfate. The solvent was distilled off under reduced pressure, giving the title compound as a colorless oil. Yield 2.3 g.

The compound obtained above (2.3 g) was dissolved in 20 ml of ethanol. To the solution was added a solution of 780 mg of L-arginine in 6 ml of water. The solvent was evaporated off under reduced pressure. To the residue was added ethanol which was evaporated off under reduced pressure, and the procedure of addition and removal of ethanol was repeated several times. To the residue was added ethyl acetate-n-hexane. The precipitated crystals were collected by filtration, giving the arginine salt of the title compound. Yield 2.5 g.

$[\alpha]_D^{18} = -92.0°$ (c=1.3, ethanol)

NMR (CD$_3$OD): δ0.90 (3H, t, J=5.5 Hz), 1.1–1.6 (16H, m), 1.6–2.3 (12H, m), 2.3–2.9 (4H, m), 3.1–3.8 (9H, m), 4.19 (2H, q, J=7 Hz) 4.2–4.4 (1H, m)

EXAMPLES 34 TO 37

The compounds as listed below in Table 10 were obtained by following the general procedure of Example 33.

mg of the β-isomer of N-[(R)-1-ethoxycarbonyl-2-pentylthioethyl]-alanyl-(S)-prolyl-(S)-proline t-butyl ester obtained in Example 32. Yield 690 mg. (free) L-Arginine salt $[\alpha]_D^{21} = -84.1°$ (c=0.5, ethanol)

NMR (CD$_3$OD): δ0.91 (3H, t, J=5.5 Hz), 1.1–1.6 (12H, m), 1.6–2.3 (12H, m), 2.4–2.9 (4H, m), 3.1–3.8 (9H, m), 4.19 (2H, q, J=7 Hz), 4.2–4.5 (1H, m)

REFERENCE EXAMPLE 31

Preparation of N-t-butoxycarbonyl-(S)-proline phenylcarbamoylmethyl ester

In 15 ml of DMF were dissolved 2.8 g of N-t-butoxycarbonyl-(S)-proline and 2.8 g of phenylcarbamoyl methyl bromide. To the solution was added 1.1 g of sodium hydrogencarbonate. The mixture was stirred at room temperature for 20 hours. The reaction mixture was poured into ice water, followed by extraction with ethyl acetate. The extract was washed with a saturated aqueous solution of sodium hydrogencarbonate and with water and dried over anhydrous sodium sulfate. The solvent was distilled off under reduced pressure and the residue was purified by silica gel column chromatography (using chloroform as an eluent), giving the title compound as a colorless oil. Yield 3.5 g.

$[\alpha]_d^{19} = -31.3°$ (c=0.7, ethanol)

TABLE 10

$$CH_3(CH_2)_6-S-\underset{\underset{CO_2C_2H_5}{|}}{\overset{(R)}{CH_2CH}}-NH-\overset{\overset{CH_3}{|}}{\underset{*}{CH}}-CO-N\underset{\phantom{xx}}{\overset{(S)}{\diagup\!\!\diagdown}}CO-NH-\overset{\overset{R_8}{|}}{\underset{(S)}{CH}}-CO_2H.\beta\text{-isomer.}\quad L\text{-arginine salt}$$

| Example No. | R$_8$ | Optical Rotation (Solvent: ethanol) | NMR(CD$_3$OD):δ |
|---|---|---|---|
| 34 | H | $[\alpha]_D^{21} = -51.3°$ (c = 1.1) | 0.90 (3H, t, J=5.5Hz), 1.1–1.6 (16H, m), 1.6–2.3 (8H, m), 2.4–3.0 (4H, m), 3.1–3.8 (7H, m), 4.19 (2H, q, J=7Hz), 4.3–4.5 (1H, m) |
| 35 | CH$_3$ | $[\alpha]_D^{21} = -58.5°$ (c = 1.7) | 0.89 (3H, t, J=5.5Hz), 1.1–1.6 (19H, m), 1.6–2.2 (8H, m), 2.4–3.0 (4H, m), 3.1–3.8 (7H, m), 4.19 (2H, q, J=7Hz) 4.3–4.6 (1H, m) |
| 36 | (CH$_3$)$_2$CH | $[\alpha]_D^{21} = -60.4°$ (c = 1.0) | 0.93 (6H, d, J= 6Hz), 1.1–1.6 (16H, m), 1.6–2.2 (8H, m), 2.4–2.9 (4H, m), 3.1–3.8 (7H, m), 4.19 (2H, q, J=7Hz), 4.4–4.6 (1H, m) |
| 37 | PhCH$_2$ | $[\alpha]_D^{18} = -29.4°$ (c = 0.8) | 0.89 (3H, t, J=5.5Hz), 1.1–1.5 (16H, m), 1.6–2.2 (8H, m), 3.0–3.8 (8H, m), 4.19 (2H, q, J=7Hz), 4.4–4.6 (1H, m), 7.19 (5H, s) |

EXAMPLE 38

Preparation of N-[(R)-1-ethoxycarbonyl-2-pentylthioethyl]-alanyl-(S)-proline (β-isomer) and L-arginine salt thereof Following the general procedure of Example 33, the title compound was prepared as a colorless oil from 890

NMR (CDCl$_3$): δ1.42 (9H, s), 3.3–3.7 (2H, m), 4.3–4.5 (1H, m), 4.68 (1H, d, J=15 Hz), 4.89 (1H, d, J=15 Hz), 7.0–7.9 (5H, m)

REFERENCE EXAMPLE 32

Preparation of N-t-butoxycarbonyl-(S)-proline phenyl ester

In 40 ml of methylene chloride were dissolved 3.0 g of N-t-butoxycarbonyl-(S)-proline, 1.3 g of phenol and 340 mg of 4-DMAP. To the solution was added with ice cooling and stirring 2.7 g of WSCD.HCl. The mixture was stirred overnight. The reaction mixture was poured into ice water, followed by extraction with ether. The extract was washed successively with 10% hydrochloric acid, water, 5% aqueous solution of sodium carbonate and water in this order and dried over anhydrous sodium sulfate. The solvent was distilled off under reduced pressure and the residue was crystallized from n-hexane. Yield 3.5 g.

$[\alpha]_D^{22} = -68.5°$ (c=0.6, ethanol)

M.p. 64° to 66° C.

REFERENCE EXAMPLES 33 TO 45

The compounds as listed below in Table 11 were obtained by following the general procedure of Reference Examples 31 and 32. In the table, Ph stands for phenyl group, Boc for t-butoxycarbonyl, and Z for benzyloxycarbonyl (these abbreviations are also used in other tables).

TABLE 11

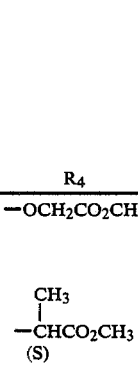

| Ref. Ex. No. | $R_A$ | $R_4$ | Optical Rotation | NMR(CDCl$_3$): δ or Melting Point |
|---|---|---|---|---|
| 33 | Boc | —OCH$_2$CO$_2$CH$_3$ | $[\alpha]_D^{17} = -75.7°$ (c = 1.9, ethanol) | 1.41, 1.46 (total 9H, each s), 3.3–3.7 (2H, m), 3.76 (3H, s) |
| 34 | Boc | —CH(CH$_3$)CO$_2$CH$_3$ (S) | $[\alpha]_D^{17} = -89.7°$ (c = 1.0, ethanol) | 1.41, 1.46 (total 9H, each s) 1.50 (3H, d, J=7Hz), 3.73 (3H, s), 5.14 (1H, q, J=7Hz) |
| 35 | Boc | —OCH$_2$CH$_2$OCH$_3$ | $[\alpha]_D^{17} = -51.1°$ (c = 1.1, ethanol) | 1.42, 1.46 (total 9H, each s), 3.37 (3H, s), 3.59 (2H, t, J=5Hz), 4.26 (2H, t, J=5Hz) |
| 36 | Boc | —OCH$_2$CCl$_3$ | $[\alpha]_D^{17} = -50.8°$ (c = 1.1, ethanol) | 1.42, 1.46 (total 9H, each s), 3.3–3.7 (2H, m), 4.61 (1H, d, J=12Hz), 4.94 (1H, d, J=12Hz) |
| 37 | Boc | —OPh | $[\alpha]_D^{22} = -68.5°$ (c = 0.6, ethanol) | 64–66° C. |
| 38 | Boc | —OCH$_2$CONH$_2$ | $[\alpha]_D^{21} = -54.2°$ (c = 0.8, ethanol) | 76–78° C. |
| 39 | Z | 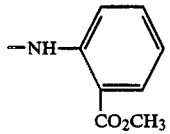 | $[\alpha]_D^{19} = -102.0°$ (c = 0.7, ethanol) | 3.83 (3H, s), 4.3–4.6 (1H, m), 5.18 (2H, s), 7.26 (5H, s), 7.0–8.1 (4H, m) |
| 40 | Boc | —NHSO$_2$CH$_3$ | $[\alpha]_D^{22} = -52.8°$ (c = 1.1, methanol) | 152–153° C. |
| 41 | Boc | —NHSO$_2$Ph | $[\alpha]_D^{22} = -30.1°$ (c = 1.1, methanol) | 186–191° C. |
| 42 | Boc | 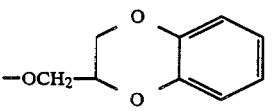 | — | 1.41, 1.46 (total 9H, each s), 4.0–4.5 (6H, m) 6.84 (4H, s) |
| 43 | Boc | 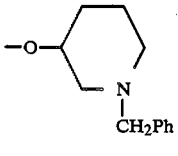 | $[\alpha]_D^{19} = -39.6°$ (c = 2.4, ethanol) | 1.38, 1.44 (total 9H, each s), 3.51 (2H, s), 4.1–4.3 (1H, m), 4.7–5.1 (1H, m), 7.28 (5H, s) |
| 44 | Boc |  | $[\alpha]_D^{20} = -27.2°$ (c = 0.7, ethanol) | 1.40, 1.44 (total 9H, each s), 2.3–2.7 (10H, m), 4.1–4.4 (4H, m), 7.1–7.5 (10H, m) |

TABLE 11-continued

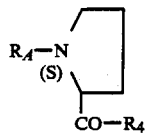

| Ref. Ex. No. | R_A | R_4 | Optical Rotation | NMR(CDCl_3): δ or Melting Point |
|---|---|---|---|---|
| 45 | Boc | α-tocopheryloxy (dl) | $[\alpha]_D^{22} = -34.1°$ (c = 1.0, methanol) | 1.48 (9H, s), 1.98 (3H, s), 2.03 (3H, s), 2.08 (3H, s), 2.58 (2H, t, J=7Hz), 3.4–3.7 (2H, m), 4.5–4.7 (1H, m) |

REFERENCE EXAMPLE 46

Preparation of (S)-proline phenyl ester hydrochloride

In 25 ml of 4N-HCl-ethyl acetate was dissolved 2.8 g of N-t-butoxycarbonyl-(S)-proline phenyl ester obtained in Reference Example 32. The solution was stirred at room temperature for 1.5 hours. The solvent was distilled off under reduced pressure. To the residue was added ethyl acetate-ether and the precipitated crystals were collected by filtration. Yield 1.9 g.

$[\alpha]_D^{22} = -22.1°$ (c=0.9, ethanol)

REFERENCE EXAMPLE 47

Preparation of N-[(R)-1-ethoxycarbonyl-2-propylthioethyl]-alanine t-butyl ester (α- and β-isomers)

In 40 ml of HMPA were dissolved 7.9 g of S-propyl-L-cysteine ethyl ester and 12.4 g of 2-bromopropionic acid t-butyl ester. To the solution was added 8.3 ml of triethylamine, and the mixture was stirred at room temperature for 40 hours. The reaction mixture was poured into ice water, followed by extraction with ethyl acetate. The extract was sufficiently washed with water and dried over anhydrous sodium sulfate. The solvent was distilled off under reduced pressure and the residue was purified by silica gel column chromatography (a 1:3 mixture of ether and n-hexane as an eluent), producing the α-isomer of the title compound as a colorless oil from the first eluate. Yield 4.4 g $[\alpha]_D^{22} = +29.9°$ (c=0.9, ethanol)

NMR (CD_3OD): δ0.98 (3H, t, J=7 Hz), 1.24 (3H, d, J=7 Hz), 1.28 (3H, t, J=7 Hz), 1.45 (9H, s), 2.53 (2H, t, J=7 Hz), 2.79 (2H, d, J=6 Hz), 4.18 (2H, q, J=7 Hz)

The β-isomer of the title compound was produced from the second eluate as a colorless oil. Yield 4.8 g.

$[\alpha]_D^{22} = -44.4°$ (c=0.7, ethanol)

NMR (CD_3OD): δ0.99 (3H, t, J=7 Hz), 1.25 (3H, d, J=7 Hz), 1.28 (3H, t, J=7 Hz), 1.47 (9H, s), 2.52 (2H, t, J=7 Hz), 4.19 (2H, q, J=7 Hz)

REFERENCE EXAMPLE 48

Preparation of N-[(R)-1-ethoxycarbonyl-2-propylthioethyl]-alanine (β-isomer)

In 15 ml of TFA was dissolved 4.7 g of the β-isomer of N-[(R)-1-ethoxycarbonyl-2-propylthioethyl]-alanine t-butyl ester obtained in Reference Example 47. The solution was stirred at room temperature for 2.5 hours. The TFA was distilled off under reduced pressure. The residue was poured into ice water, adjusted to a pH of 4 with a saturated aqueous solution of sodium hydrogencarbonate and extracted with methylene chloride. The extract was washed with water and dried over anhydrous sodium sulfate. The solvent was distilled off under reduced pressure. To the residue was added ether and the precipitated crystals were collected by filtration. The crystals were recrystallized from methylene chloride-ether, giving the β-isomer of the title compound. Yield 1.9 g.

NMR (CD_3OD): δ1.00 (3H, t, J=7 Hz), 1.31 (3H, t, J=7 Hz), 1.46 (3H, d, J=7 Hz), 2.57 (2H, t, J=7 Hz), 3.52 (1H, q, J=7 Hz), 4.27 (2H, q, J=7 Hz)

EXAMPLE 39

Preparation of N-[(R)-1-ethoxycarbonyl-2-propylthioethyl]-alanyl-(S)-proline methoxycarbonylmethyl ester (β-isomer) and maleate thereof Following the general procedure of Reference Example 46, (S)-proline methoxycarbonylmethyl ester hydrochloride (440 mg) was produced from 650 mg of N-t-butoxycarbonyl-(S)-proline methoxycarbonylmethyl ester obtained in Reference Example 33. In 10 ml of DMF were dissolved 430 mg of the β-isomer of N-[(R)-1-ethoxycarbonyl-2-propylthioethyl]-alanine obtained in Reference Example 48 and 440 mg of (S)-proline methoxycarbonylmethyl ester hydrochloride. To the solution was added a solution of 360 mg of DEPC (90% content) in 2 ml of DMF with ice cooling and stirring. Further a solution of 0.51 ml of triethylamine in 2 ml of DMF was added dropwise to the solution. The solution was stirred with ice cooling for 2 hours and then further stirred at room temperature for 10 hours. The reaction mixture was poured into ice water and the mixture was extracted with ethyl acetate. The extract was sufficiently washed with water and dried over anhydrous sodium sulfate. The solvent was distilled off under reduced pressure. The residue was purified by silica gel column chromatography (a 40:1 mixture of chloroform and methanol as an eluent), giving the β-isomer of the title compound as a colorless oil. Yield 610 mg.

The compound obtained above (610 mg) was dissolved in 25 ml of ethyl acetate. In the solution was dissolved 163 mg of maleic acid and the solvent was evaporated under reduced pressure. To the residue was added ether and the precipitated crystals were collected by filtration. The crystals were reprecipitated from ethyl acetate-ether, giving maleate of the β-isomer of the title compound. Yield 507 mg.

$[\alpha]_D^{25} = -80.0°$ (c=0.5, methanol)

M.p. 107° to 108° C.

EXAMPLE 40

Preparation of N-[(R)-1-ethoxycarbonyl-2-heptylthioethyl]-alanyl-(S)-proline 2-methoxycarbonylphenylamide (β-isomer) and maleate thereof In 20 ml of ethanol was dissolved 1.9 g of N-benzyloxycarbonyl-(S)-proline 2-methoxycarbonylphenylamide (β-isomer) and maleate thereof In 20 ml of ethanol was dissolved 1.9 g of N-benzyloxycarbonyl-(S)-proline 2-methoxycarbonylphenylamide prepared in Reference Example 39. To the solution was added 1 g of 10% Pd-carbon and the mixture was hydrogenated at ambient temperature and under atomspheric pressure. After 1.5 hours, the catalyst was removed by filtration and the filtrate was distilled off under reduced pressure. To the residue was added ether. The precipitated crystals were collected by filtration, giving 950 mg of (S)-proline 2-methoxycarbonylphenylamide.

In 20 ml of DMF were dissolved 1.1 g of the β-isomer of N-[(R)-1-ethoxycarbonyl-2-heptylthioethyl]-alanine prepared in Reference Example 29(b), 890 mg of (S)-proline 2-methoxycarbonylphenylamide, 760 mg of WSCD.HCl and 490 mg of HOBt. To the solution was added 0.5 ml of triethylamine with ice cooling and stirring. The solution was stirred overnight. The reaction mixture was poured into ice water, followed by extraction with ethyl acetate. The extract was sufficiently washed with water and dried over anhydrous sodium sulfate. The solvent was evaporated under reduced pressure and the residue was purified by silica gel column chromatography (a 30:1 mixture of chloroform and methanol as an eluent), giving the β-isomer of the title compound as a colorless oil. Yield 1.6 g.

The compound obtained above (1.6 g) was dissolved in 50 ml of ethyl acetate. In the solution was dissolved 350 mg of maleic acid and the solvent was evaporated under reduced pressure. To the residue was added ether and the precipitated crystals were collected by filtration. The crystals were recrystallized from ethyl acetate-ether, affording maleate of the β-isomer of the title compound. Yield 1.2 g.

$[\alpha]_D^{21} = -92.3°$ (c=0.8, ethanol)
M.p. 118° to 120° C.

EXAMPLES 41 TO 55

The compounds as listed below in Table 12 were obtained by following the general procedure of Examples 39 and 40.

TABLE 12

$$CH_3(CH_2)_6SCH_2\overset{(R)}{C}H-NH-\overset{CH_3}{\underset{*}{C}H}-CO-N\underset{(S)}{\diagdown}\underset{COR_4}{\diagup} \quad \beta\text{-isomer}$$
$$\underset{CO_2C_2H_5}{|}$$

| Example No. | R₄ | Salt | Optical Rotation | NMR (CD₃OD):δ or Melting point or Mass spectrometry |
|---|---|---|---|---|
| 41 | —OCH₂CO₂CH₃ | maleate | $[\alpha]_D^{19} = -77.8°$ (c = 0.8, ethanol) | 91–93° C. |
| 42 | —CH(CH₃)CO₂CH₃ (S) | maleate | $[\alpha]_D^{24} = -80.5°$ (c = 0.7, ethanol) | 75–98° C. |
| 43 | —OCH₂CH₂OCH₃ | maleate | $[\alpha]_D^{24} = -64.1°$ (c = 0.7, ethanol) | 65–67° C. |
| 44 | —OCH₂CCl₃ | maleate | $[\alpha]_D^{24} = -62.9°$ (c = 0.8, ethanol) | 104–106° C. |
| 45 | —OCH₂CH(CH₃)NH—COC(O)C(CH₃)₃ (S) | maleate | — | 55–59° C. |
| 46 | —O—C₆H₅ | maleate | $[\alpha]_D^{22} = -73.9°$ (c = 0.6, ethanol) | 100–102° C. |
| 47 | —OCH₂CONH₂ | maleate | $[\alpha]_D^{21} = -59.9°$ (c = 0.6, ethanol) | 127–129° C. |
| 48 | —NH₂ | maleate | $[\alpha]_D^{23} = -59.2°$ (c = 0.7, ethanol) | 105–107° C. |
| 49 | —OCH₂CONH—C₆H₅ | maleate | $[\alpha]_D^{21} = -50.7°$ (c = 0.6, ethanol) | 101–103° C. |
| 50 | —NHSO₂CH₃ | maleate | $[\alpha]_D^{25} = -64.0°$ (c = 1.2, methanol) | 116–121° C. |

TABLE 12-continued $$CH_3(CH_2)_6SCH_2\overset{(R)}{\underset{|}{CH}}-NH-\overset{CH_3}{\underset{*}{\overset{|}{CH}}}-CO-N\overset{(S)}{\diagdown}\diagup \text{ .}\beta\text{-isomer}$$
$$\phantom{CH_3(CH_2)_6SCH_2}\underset{CO_2C_2H_5}{|}\phantom{-NH-CH-CO-N}\underset{COR_4}{\diagdown\diagup}$$

| Example No. | R₄ | Salt | Optical Rotation | NMR (CD₃OD):δ or Melting point or Mass spectrometry |
|---|---|---|---|---|
| 51 | —NHSO₂—(phenyl) | hydrochloride | $[\alpha]_D^{25} = -105.6°$ (c = 1.4, methanol) | 142–150° C. |
| 52 | —OCH₂—(benzodioxane) | maleate | $[\alpha]_D^{17} = -56.2°$ (c = 0.8, ethanol) | 70–82° C. |
| 53 | —O—(N-benzyl piperidine) | dihydrochloride | $[\alpha]_D^{19} = -34.9°$ (c = 1.0, ethanol) | 74–86° C |
| 54 | —OCH₂CH₂—N(piperazinyl)N—CH(Ph)(Ph) | trihydrochloride | $[\alpha]_D^{19} = -12.5°$ (c = 0.9, ethanol) | 0.90 (3H, t, J=5.5Hz), 1.63, 1.60 (total 3H, each d, J=7Hz), 2.59 (2H, t, J=7Hz), 7.3–8.1 (10H, m) |
| 55 | α-tocopheryloxy (dl) | hydrochloride | $[\alpha]_D^{22} = -34.2°$ (c = 0.7, ethanol) | m/Z: 828, 755, 683, 430 |
| 62 | —OCH₂—(pyridyl) | maleate | $[\alpha]_D^{22} = -63.8°$ (c = 0.6, ethanol) | 112–114.5° C. |

REFERENCE EXAMPLE 49

Preparation of N-[(R)-1-ethoxycarbonyl-2-cyclooctylthioethyl]-alanine t-butyl ester (α- and β-isomers)

The title compounds were prepared by following the general procedure of Reference Example 1.

α-isomer
$[\alpha]_D^{22} = +26.8°$ (c=0.9, ethanol)
NMR (CDCl₃): δ1.28 (3H, d, J=7 Hz), 1.29 (3H, t, J=7 Hz), 1.45 (9H, s), 1.4–2.1 (15H, m), 2.34 (1H, brs), 2.81 (2H, d, J=6 Hz), 3.33 (1H, q, J=7 Hz), 3.46 (1H, t, J=6 Hz), 4.20 (2H, q, J=7 Hz), β-isomer
$[\alpha]_D^{22} = -31.5°$ (c=1.0, ethanol)
NMR (CDCl₃): δ1.30 (3H, d, J=7 Hz), 1.30 (3H, t, J=7 Hz), 1.47 (9H, s), 1.4–2.1 (15H, m), 2.24 (1H, brs), 2.5–3.2 (2H, m), 3.2–3.6 (2H, m), 4.21 (2H, q, J=7 Hz)

REFERENCE EXAMPLE 50

Preparation of N-[(R)-1-ethoxycarbonyl-2-cyclooctylthioethyl]-alanine (α- and β-isomers)

Following the general procedure of Reference Example 8, the title compounds (α- and β-isomers) were prepared respectively from the α- and β-isomers of N-[(R)-1ethoxycarbonyl-2-cyclooctylthioethyl]-alanine t-butyl ester obtained in Reference Example 49.

α-isomer
$[\alpha]_D^{23} = +21.6°$ (c=0.5, DMF)
M.p. 102° to 106° C.

β-isomer
$[\alpha]_D^{23} = -18.9°$ (c=0.5, DMF)
M.p. 139° to 143° C.

EXAMPLE 56

Preparation N-[(R)-1-ethoxycarbonyl-2-cyclooctylthioethyl]-alanyl-(S)-proline methyl ester (β-isomer) maleate Following the general procedure of Example 39, the title compound was prepared from the β-isomer of N-[(R)-1-ethoxycarbonyl-2-cyclooctylthioethyl]-alanine prepared in Reference Example 50 and (S)-proline methyl ester hydrochloride.
$[\alpha]_D^{23} = -57.2°$ (c=0.4, methanol)
M.p. 116° to 117° C.

EXAMPLES 57 AND 58

The compounds as listed below in Table 13 were obtained by following the general procedure of Example 56.

TABLE 13

$$R_1-S-CH_2\overset{(R)}{\underset{COOC_2H_5}{CH}}-NH-\overset{CH_3}{\underset{*}{\overset{|}{CH}}}-CO-N\overset{(S)}{\underset{COOCH_3}{\diagdown}}\diagup \quad \cdot maleate$$

| Example No. | $R_1$ | Isomer (*) | Optical Rotation | Melting point (°C.) |
|---|---|---|---|---|
| 57 | (cyclopentyl) | β | $[\alpha]_D^{22} = -68.4°$ (c = 0.5, ethanol) | 111–113 |
| 58 | (indanyl) | β | $[\alpha]_D^{23} = -56.3°$ (c = 0.9, ethanol) | 115–116 |

EXAMPLE 59

Preparation of
N-[(R)-1-carboxy-2-cyclopentylthioethyl]-alanyl-(S)-proline (β-isomer)

A 300 mg portion of maleate of β-isomer of N-[(R)-1-ethoxycarbonyl-2-cyclopentylthioethyl]-alanyl-(S)-proline methyl ester prepared in Example 57 was dissolved in 2 ml of ethanol. To the solution was added dropwise 2.9 ml of 1N-NaOH at room temperature. The mixture was stirred overnight and neutralized with 2N-HCl with ice cooling. The solvent was completely removed by distillation. The residue was dissolved in methanol and the solution was subjected to high performance liquid chromatography (column=Chemcosorb 7-ODS-H, eluent=a 50:50:0.4 mixture of methanol, water and acetic acid) for separation. The solvent was distilled off. After addition of 4 ml of ether, the precipitated crystals were collected by filtration, giving the title compound as white crystals. Yield 160 mg.

$[\alpha]_D^{22} = -98.0°$ (c=0.1, methanol)
M.p. 85° to 95° C.

EXAMPLE 60

Preparation of
N-[(R)-1-carboxy-2-(2-indanyl)thioethyl]-alanyl-(S)-proline (β-isomer)

Following the general procedure of Example 59, the title compound was prepared as white crystals from 300 mg of the maleate of β-isomer of N-[(R)-1-ethoxycarbonyl-2(2-indanyl)thioethyl]-alanyl-(S)-proline methyl ester prepared in Example 58. Yield 165 mg.

$[\alpha]_D^{22} = -78°$ C.

EXAMPLE 61

Preparation of
N-[(R)-1-ethoxycarbonyl-2-heptylthioethyl]-alanyl-(S)-prolyl-(S)-phenylalanine methyl ester (β-isomer) maleate Following the general procedure of Example 39, the title compound was prepared from N-[(R)-1-ethoxycarbonyl-2-heptylthioethyl]-alanine (β-isomer) obtained in Reference Example 29 and (S)-prolyl-(S)-phenylalanine methyl ester hydrochloride.

$[\alpha]_D^{23} = -41.9°$ (c=0.8, ethanol)
NMR (CD₃OD): δ0.90 (3H, t, J=5 Hz), 1.32 (3H, t, J=7 Hz), 1.52 (3H, d, J=7 Hz), 2.58 (2H, t, J=7 Hz), 3.65 (3H, s), 4.29 (2H, q, J=7 Hz), 6.26 (2H, s), 7.24 (5H, s)

PREPARATION EXAMPLE 1—PREPARATION OF TABLETS

One thousand tablets for oral administration each containing 5 mg of maleate of N-[(R)-1-ethoxycarbonyl-2-heptylthioethyl]-alanyl-(S)-proline methoxycarbonylmethyl ester (β-isomer) were prepared according to the following formulation.

| Component | Amount (g) |
|---|---|
| Maleate of N—[(R)-1-ethoxycarbonyl-2-heptylthioethyl]-alanyl-(S)—proline methoxycarbonylmethyl ester (β-isomer) | 5 |
| Lactose (according to Japanese Pharmacopoeia) | 50 |
| Corn starch (according to Japanese Pharmacopoeia) | 25 |
| Crystalline cellulose (according to Japanese Pharmacopoeia) | 25 |
| Methyl cellulose (according to Japanese Pharmacopoeia) | 1.5 |
| Magnesium stearate (according to Japanese Pharmacopoeia) | 1 |

The maleate of N-[(R)-1-ethoxycarbonyl-2-heptylthioethyl]-alanyl-(S)-proline methoxycarbonylmethyl ester (β-isomer), lactose, corn starch and crystalline cellulose were thoroughly mixed together and granulated with a 5% aqueous solution of methyl cellulose. The granules thus obtained were passed through a 200-mesh sieve and mixed with magnesium stearate and the mixture was pressed into tablets.

PREPARATION EXAMPLE 2—PREPARATION OF CAPSULES

One thousand hard gelatin capsules for oral administration each containing 10 mg of maleate of N-[(R)-1-ethoxycarbonyl-2-heptylthioethyl]-alanyl-(S)-proline 2-methoxyethyl ester (β-isomer) were prepared according to the following formulation.

| Component | Amount (g) |
|---|---|
| Maleate of N—[(R)-1-ethoxycarbonyl-2-heptylthioethyl]-alanyl-(S)—proline 2-methoxyethyl ester | 10 |

| Component | Amount (g) |
| --- | --- |
| (β-isomer) | |
| Lactose (according to Japanese Pharmacopoeia) | 80 |
| Starch (according to Japanese Pharmacopoeia) | 30 |
| Talc (according to Japanese Pharmacopoeia) | 5 |
| Magnesium stearate (according to Japanese Pharmacopoeia) | 1 |

The foregoing components were finely divided and thoroughly stirred to obtain a homogeneous mixture. The mixture was enclosed in capsules for oral administration having the desired size.

PREPARATION EXAMPLE 3—PREPARATION OF INJECTIONS

A sterilized aqueous solution for parenteral administration was prepared according to the following formulation.

| Component | Amount (g) |
| --- | --- |
| N—[(R)-1-ethoxycarbonyl-2-heptyl-thioethyl]-alanyl-(S)—proline 1-phenylmethyl-3-piperidyl ester (β-isomer) dihydrochloride | 1 |
| Polyethylene glycol having a molecular weight of 4,000 (according to Japanese Pharmacopoeia) | 0.3 |
| Sodium chloride (according to Japanese Pharmacopoeia) | 0.9 |
| Polyoxyethylene sorbitan monooleate (according to Japanese Pharmacopoeia) | 0.4 |
| Sodium metabisulfite (according to Japanese Pharmacopoeia) | 0.1 |
| Methylparaben (according to Japanese Pharmacopoeia) | 0.18 |
| Propylparaben (according to Japanese Pharmacopoeia) | 0.02 |
| Distilled water for injection | 100 (ml) |

The foregoing parabens, sodium metabisulfite and sodium chloride were dissolved at 80° C. in about 50 ml of distilled water for injection while being stirred. The solution was cooled to 40° C. In the solution were dissolved N-[(R)-1-ethoxycarbonyl-2-heptylthioethyl]-alanyl-(S)-proline 1-phenylmethyl-3-piperidyl ester (β-isomer) dihydrochloride, polyethylene glycol and polyoxyethylene sorbitan monooleate. Distilled water for injection (about 50 ml) was added to the solution to adjust the final regulated volume, and the mixture was sterilized by sterile filtration using suitable filter paper. One mililiter of the solution was introduced into separate ampoules to make injectables.

PREPARATION EXAMPLE 4—PREPARATION OF TABLETS

One thousand tablets for oral administration each containing 5 mg of maleate of N-[(R)-1-ethoxycarbonyl-2-cyclopentylthioethyl]-alanyl-(S)-proline methyl ester (β-isomer) were prepared according to the following formulation.

| Component | Amount (g) |
| --- | --- |
| N—[(R)-1-ethoxycarbonyl-2-cyclo-pentylthioethyl]-alanyl-(S)—proline methyl ester (β-isomer) maleate | 5 |
| Lactose (according to Japanese Pharmacopoeia) | 50 |
| Corn starch (according to Japanese Pharmacopoeia) | 25 |
| Crystalline cellulose (according to Japanese Pharmacopoeia) | 25 |
| Methyl cellulose (according to Japanese Pharmacopoeia) | 1.5 |
| Magnesium stearate (according to Japanese Pharmacopoeia) | 1 |

N-[(R)-1-ethoxycarbonyl-2-cyclopentylthioethyl]-alanyl-(S)- proline methyl ester (β-isomer) maleate, lactose, corn starch and crystalline cellulose were thoroughly mixed together and granulated with a 5% aqueous solution of methyl cellulose. The granules thus obtained were passed through a 200-mesh sieve and mixed with magnesium stearate and the mixture was pressed into tablets.

PREPARATION EXAMPLE 5—PREPARATION OF TABLETS

One thousand tablets for oral administration each containing 5 mg of N-[(R)-1-ethoxycarbonyl-2-(2-indanylthio)ethyl]-alanyl-(S)-proline methyl ester (β-isomer) maleate were prepared according to the following formulation.

| Component | Amount (g) |
| --- | --- |
| Maleate of N—[(R)-1-ethoxycarbonyl-2-(2-indanylthio)ethyl]-alanyl-(S)—proline methyl ester (β-isomer) | 5 |
| Lactose (according to Japanese Pharmacopoeia) | 50 |
| Corn starch (according to Japanese Pharmacopoeia) | 25 |
| Crystalline cellulose (according to Japanese Pharmacopoeia) | 25 |
| Methyl cellulose (according to Japanese Pharmacopoeia) | 1.5 |
| Magnesium stearate (according to Japanese Pharmacopoeia) | 1 |

N-[(R)-1-ethoxycarbonyl-2-(2-indanylthio)ethyl]-alanyl-(S)- proline methyl ester (β-isomer) maleate, lactose, corn starch and crystalline cellulose were thoroughly mixed together and granulated with a 5% aqueous solution of methyl cellulose. The granules thus obtained were passed through a 200-mesh sieve and mixed with magnesium stearate and the mixture was pressed into tablets.

PREPARATION EXAMPLE 6—PREPARATION OF TABLETS

One thousand tablets for oral administration each containing 5 mg of maleate of N-[(R)-1-ethoxycarbonyl-2-heptylthioethyl]-alanyl-(S)-prolyl-(S)-phenylalanine methyl ester (β-isomer) were prepared according to the following formulation.

| Component | Amount (g) |
| --- | --- |
| N—[(R)-1-ethoxycarbonyl-2-heptyl-thioethyl]-alanyl-(S)—prolyl-(S)—phenylalanine methyl ester (β-isomer) maleate | 5 |
| Lactose (according to Japanese Pharmacopoeia) | 50 |
| Corn starch (according to Japanese Pharmacopoeia) | 25 |

| Component | Amount (g) |
| --- | --- |
| Crystalline cellulose (according to Japanese Pharmacopoeia) | 25 |
| Methyl cellulose (according to Japanese Pharmacopoeia) | 1.5 |
| Magnesium stearate (according to Japanese Pharmacopoeia) | 1 |

The maleate of N-[(R)-1-ethoxycarbonyl-2-heptylthioethyl]-alanyl-(S)-prolyl-(S)-phenylalanine methyl ester (β-isomer), lactose, corn starch and crystalline cellulose were thoroughly mixed together and granulated with a 5% aqueous solution of methyl cellulose. The granules thus obtained were passed through a 200-mesh sieve and mixed with magnesium stearate and the mixture was pressed into tablets.

PHARMACOLOGICAL TEST 1

INHIBITORY ACTIVITY AGAINST ANGIOTENSIN-CONVERTING ENZYME (ACE)

A 100 μl quantity of an enzyme solution prepared from rabbit lung acetone powder (product of Sigma Chemical Co., Ltd., U.S.A.) was mixed with 100 μl of a sample solution. The mixture was gently shaken at 37° C. for 10 minutes. To the reaction mixture was added 100 μl of a solution containing 6.69 mM of hippuryl-histidyl-lecuine (product of Peptide Institute, Inc., Japan) as a substrate. The mixture was reacted at 37° C. for 45 minutes while being shaken. The reaction was terminated by addition of 200 μl of a 1N sulfuric acid to the reaction mixture. Sodium chloride (saturation amount) and diethyl ether (2 ml) were added to the reaction mixture to extract the hippuric acid formed by the reaction. The resulting mixture was vigorously shaken for 15 minutes and centrifuged at 2000 r.p.m. for 5 minutes. A 1.5 ml quantity of the ether layer was separated. After the solvent was distilled off, the residue was redissolved in 1.5 ml of distilled water and the absorbance of 228 nm was measured. A control was prepared by repeating the same procedure as above except that 100 μm of distilled water was used in place of the sample solution.

The inhibitory activity was calculated by deducting the absorbance value of the residue formed by addition of the sample solution from that of the control and the resulting value was divided by the absorbance value of the control and multipled by 100, thereby giving a percent inhibition. The inhibitory activity was expressed as $IC_{50}$, i.e., the concentration of the same sample solution in the reaction mixture in which concentration 50% inhibition is achieved.

The test compounds used in the experiment are shown below in Table 14 together with the test result.

TABLE 14

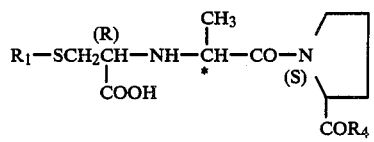

$$R_1-SCH_2\overset{(R)}{C}H-NH-\overset{CH_3}{\underset{*}{C}H}-CO-N\overset{(S)}{\diagdown}$$
$$\underset{COOH}{\mid} \qquad \qquad \underset{COR_4}{}$$

| Compound No. | $R_1$ | $R_4$ | Isomer (*) | ACE inhibitory activity $IC_{50}$ (mol/liter) |
| --- | --- | --- | --- | --- |
| 1 | 1-methylcyclohexyl | —OH | β | $5.21 \times 10^{-9}$ |
| 2 | indan-2-yl | —OH | β | $6.87 \times 10^{-10}$ |
| 3 | cyclopentyl | —OH | β | $1.02 \times 10^{-9}$ |
| 4 | cyclopentyl-NHC(O)CH₂— | —OH | β | $6.11 \times 10^{-8}$ |
| 5 | $C_6H_5CH_2NHC(O)CH_2-$ | —OH | (R,S) | $3.42 \times 10^{-7}$ |
| 6 | cyclohexyl-NC(O)CH₂— | —OH | (R,S) | $4.43 \times 10^{-7}$ |
| 7 | $CH_3(CH_2)_6-$ | $-NHCH(CH_2C_6H_5)-COOH$ | β | $2.41 \times 10^{-8}$ |

TABLE 14-continued

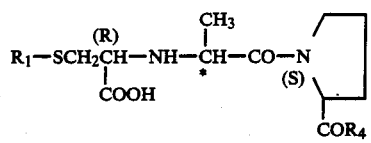

| Compound No. | $R_1$ | $R_4$ | Isomer (*) | ACE inhibitory activity $IC_{50}$ (mol/liter) |
|---|---|---|---|---|
| 8 | $CH_3(CH_2)_6-$ | $-NHCH-COOH$<br>$\quad\quad\,\,\vert$<br>$\quad\quad CH_3$ | β | $5.63 \times 10^{-8}$ |
| 9 | $CH_3(CH_2)_6-$ | $-NHCH-COOH$<br>$\quad\quad\,\,\vert$<br>$\quad\quad CH(CH_3)_2$ | β | $3.35 \times 10^{-8}$ |

Table 14 reveals that the compounds of this invention have outstanding inhibitory activity against the angiotensin-converting enzyme.

We claim:

1. A proline derivative represented by the formula

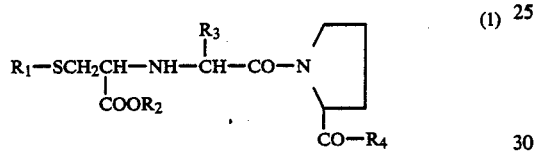

(1)

wherein:
$R_1$ is adamantyl, indanyl, 1,2,3,4-tetrahydro-naphthyl or cycloalkyl having 3 to 8 carbon atoms and optionally substituted with lower alkyl, or $R_1$ is $C_1$-$C_9$ alkyl or a group

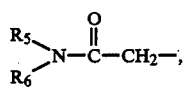

wherein $R_5$ and $R_6$ are the same or different and each represent hydrogen, lower alkyl, phenyl, phenyl-lower alkyl, naphthyl or cycloalkyl having 3 to 8 carbon atoms, or $R_5R_6N-$ is

wherein R is alkylene having 3 to 8 carbon atoms;
$R_2$ is hydrogen or lower alkyl;
$R_3$ is lower alkyl; and
$R_4$ is hydroxy, lower alkoxy, a group

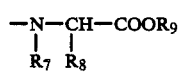

wherein $R_7$ is hydrogen and $R_8$ is hydrogen, lower alkyl or phenyl-lower alkyl, or $R_7$ and $R_8$ are taken together and form $C_2$-$C_4$ alkylene bridge, and $R_9$ is hydrogen or lower alkyl, or substituted lower alkoxy wherein the substituent is selected from the group consisting of lower alkoxy, lower alkoxycarbonyl, halogen, carbamoyl, monophenylcarbamoyl, N,N-diphenylcarbamoyl, α-naphthylcarbamoyl, β-naphthylcarbamoyl, pyridyl, a group

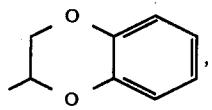

4 -(1,1-diphenylmethyl)-1-piperazinyl and lower alkoxycarbonylamino, or $R_4$ is phenyloxy, α-naphthyloxy, β-naphthyloxy, tocopheryloxy, 1-(phenyl-lower alkyl)-piperidyloxy, amino, lower alkoxy-carbonyl-substituted phenylamino, lower alkyl sulfonylamino, pihenylsulfonylamino, p-toluenesulfonylamino, α-naphthylsulfonylamino, or β-naphthylsulfonylamino, with the proviso that $R_4$ is not hydroxy or lower alkoxy when $R_1$ is $C_1$-$C_9$ alkyl;

2. A proline derivative as defined in claim 1 wherein $R_1$ is indanyl, 1,2,3,4-tetrahydronaphthyl or cycloalkyl having 3 to 8 carbon atoms and optionally substituted with lower alkyl.

3. A proline derivative as defined in claim 1 wherein $R_1$ is indanyl or $C_5$-$C_8$ cycloalkyl.

4. A proline derivative as defined in claim 1 wherein $R_1$ is indanyl, 1,2,3,4-tetrahydronaphthyl or cycloalkyl having 3 to 8 carbon atoms optionally substituted with lower alkyl and $R_4$ is hydroxy, lower alkoxy or substituted lower alkoxy wherein the substituent is selected from the group consisting of lower alkoxy, lower alkoxycarbonyl, halogen and a group

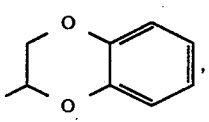

1-(phenyl-lower alkyl)-piperidyloxy, tocopheryloxy or a group

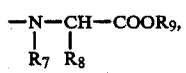

wherein $R_7$ is hydrogen, $R_8$ is phenyl-lower alkyl and $R_9$ is lower alkyl.

5. A proline derivative as defined in claim 1 wherein $R_1$ is indanyl or $C_5$-$C_8$ cycloalkyl and $R_4$ is hydroxy, lower alkoxy or substituted lower alkoxy wherein the substituent is selected from the group consisting of lower alkoxy, lower alkoxycarbonyl, halogen and a group

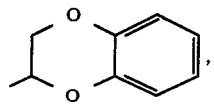

(phenyl-lower alkyl)-piperidyloxy, tocopheryloxy or a group

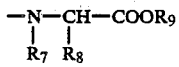

(wherein $R_7$ is hydrogen, $R_8$ is phenyl-lower alkyl and $R_9$ is lower alkyl).

6. A proline derivative as defined in claim 1 wherein $R_1$ is indanyl or cyclopentyl, $R_2$ is lower alkyl, $R_3$ is methyl and $R_4$ is hydroxy, methoxy, 1-benzyl-3-piperidyloxy, tocopheryloxy, a group —NH—CH(CH$_2$C$_6$H$_5$)—COOCH$_3$, trihalogenomethoxy, or methoxy or ethoxy group which is substituted with one member selected from the group consisting of methoxy, methoxycarbonyl and a group

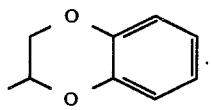

7. A proline derivative as defined in claim 1 wherein $R_1$ is $C_1$–$C_9$ alkyl.

8. A proline derivative as defined in claim 1 wherein $R_1$ is $C_7$–$C_9$ alkyl.

9. A proline derivative as defined in claim 1 where $R_1$ is $C_1$–$C_9$ alkyl, and $R_4$ is substituted lower alkoxy wherein the substituent is selected from the group consisting of lower alkoxy, lower alkoxycarbonyl, halogen and a group

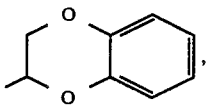

(phenyl-lower alkyl)-piperidyloxy, tocopheryloxy or a group

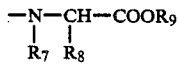

(wherein $R_7$ is hydrogen, $R_8$ is phenyl-lower alkyl and $R_9$ is lower alkyl).

10. A proline derivative as defined in claim 1 wherein $R_1$ is $C_7$–$C_9$ alkyl, $R_2$ is lower alkyl and $R_4$ is substituted lower alkoxy wherein the substituent is selected from the group consisting of lower-alkoxy, lower alkoxycarbonyl, halogen and a group

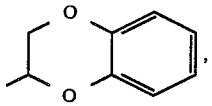

1-(phenyl-lower alkyl)-piperidyloxy, tocopheryloxy or a group

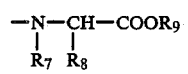

(wherein $R_7$ is hydrogen, $R_8$ is phenyl-lower alkyl and $R_9$ is lower alkyl).

11. A proline derivative as defined in claim 1 wherein $R_1$ is $C_7$ alkyl, $R_2$ is lower alkyl, $R_3$ is methyl and $R_4$ is 1-benzyl-3-piperidyloxy, tocopheryloxy, a group —NH—CH(CH$_2$C$_6$H$_5$)—COOCH$_3$, trihalogenomethoxy, or methoxy or ethoxy group which is substituted with one member selected from the group consisting of methoxy, methoxycarbonyl, and a group

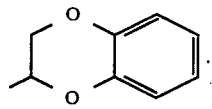

12. A proline derivative as defined in claim wherein $R_1$ is indanyl, $R_2$ is lower alkyl and $R_4$ is hydroxy or lower alkoxy.

13. A proline derivative as defined in claim 1 wherein $R_1$ is $C_5$–$C_8$ cycloalkyl, $R_2$ is lower alkyl and $R_4$ is hydroxyl or lower alkoxy.

14. A proline derivative as defined in claim 1 which is N-[(R)-1-ethoxycarbonyl-2-(2-cyclopentylthioethyl]-alanyl-(S)-proline methyl ester (β-isomer).

15. A proline derivative as defined in claim 1 which is N-[(R)-1-ethoxycarbonyl-2-(2indanylthio)ethyl]-alanyl-(S)-proline methyl ester (β-isomer).

16. A proline derivative as defined in claim 1 which is N-[(R)-1-ethoxycarbonyl-2-heptylthioethyl]-alanyl-(S)-prolyl-(S)-phenylalanine methyl ester (β-isomer).

17. A proline derivative as defined in claim 1 which is N-[(R)-1-ethoxycarbonyl-2-heptylthioethyl]-alanyl-(S)-proline 1-phenylmethyl-3-piperidyl ester (β-isomer).

18. A proline derivative as defined in claim 1 which is N-[(R)-1-ethoxycarbonyl-2-heptylthioethyl]-alanyl-(S)-proline methoxycarbonylmethyl ester (β-isomer).

19. A proline derivative as defined in claim 1 which is N-[(R)-1-ethoxycarbonyl-2-cyclopentylthioethyl]-alanyl-(S)-proline 2-methoxyethyl ester (β-isomer).

20. A pharmaceutical composition for inhibiting angiotensin converting enzyme comprising an effective amount of at least one of the proline derivative and pharmaceutically acceptable salt thereof as defined in claim 1 in combination with a pharmaceutically acceptable carrier.

21. A method for inhibiting angiotensin converting enzyme comprising administering to a patient at least one of the proline derivative and pharmaceutically acceptable salt thereof as defined in claim 1 in an amount effective for inhibiting the angiotensin converting enzyme.

* * * * *